US009107957B2

(12) United States Patent
Rozema et al.

(10) Patent No.: US 9,107,957 B2
(45) Date of Patent: *Aug. 18, 2015

(54) PEPTIDE-BASED IN VIVO SIRNA DELIVERY SYSTEM

(71) Applicant: Arrowhead Madison Inc., Madison, WI (US)

(72) Inventors: David B Rozema, Middleton, WI (US); David L Lewis, Madison, WI (US); Darren Wakefield, Fitchburg, WI (US); Eric Kitas, Aesch (CH); Philipp Hadwiger, Kulmbach (DE); Jon Wolff, Madison, WI (US); Ingo Röhl, Memmelsdorf (DE); Peter Mohr, Basel (CH); Torsten Hoffmann, Weil am Rhein (DE); Kerstin Jahn-Hofmann, Neu-Isenburg (DE); Hans Martin Mueller, Munich (DE); Günther Ott, Bayreuth (DE); Andrei V Blokhin, Fitchburg, WI (US); Jonathan D Benson, Stoughton, WI (US); Jeffrey C Carlson, Madison, WI (US)

(73) Assignee: Arrowhead Madison Inc., Madison, WI (US)

( * ) Notice: Subject to any disclaimer, the term of this patent is extended or adjusted under 35 U.S.C. 154(b) by 66 days.

This patent is subject to a terminal disclaimer.

(21) Appl. No.: 13/926,380

(22) Filed: Jun. 25, 2013

(65) Prior Publication Data

US 2013/0281658 A1    Oct. 24, 2013

Related U.S. Application Data

(63) Continuation of application No. 13/326,433, filed on Dec. 15, 2011, now Pat. No. 8,501,930.

(60) Provisional application No. 61/424,191, filed on Dec. 17, 2010.

(51) Int. Cl.
| | | |
|---|---|---|
| *C07H 21/04* | (2006.01) | |
| *C07H 21/02* | (2006.01) | |
| *C07K 5/00* | (2006.01) | |
| *A61K 47/48* | (2006.01) | |
| *C12N 15/11* | (2006.01) | |

(52) U.S. Cl.
CPC ..... *A61K 47/48261* (2013.01); *A61K 47/48092* (2013.01); *A61K 47/48246* (2013.01); *C12N 15/111* (2013.01); *C12N 2310/14* (2013.01); *C12N 2310/351* (2013.01); *C12N 2310/3515* (2013.01); *C12N 2320/32* (2013.01)

(58) Field of Classification Search
CPC ..................................................... C12N 15/113
See application file for complete search history.

(56) References Cited

U.S. PATENT DOCUMENTS

| | | |
|---|---|---|
| 2003/0130189 A1 | 7/2003 | Senter et al. |
| 2003/0220264 A1 | 11/2003 | Rozema et al. |
| 2004/0162235 A1 | 8/2004 | Trubetskoy et al. |
| 2009/0131360 A1 | 5/2009 | Woolf et al. |
| 2009/0169638 A1 | 7/2009 | Davis et al. |
| 2012/0100569 A1* | 4/2012 | Liu et al. ............. 435/29 |

FOREIGN PATENT DOCUMENTS

WO      WO 2010/129672 A1     11/2010

OTHER PUBLICATIONS

Chen et al. "Synthetic PEGylated Glycoproteins and their Utility in Gene Delivery." Bioconjugate Chemistry 2007 18(2): 371-378.
Findeis MA: "Stepwise Synthesis of a Galnac-Containing Cluster Glycoside Ligand of the Asialoglycoprotein Receptor", International Journal of Peptide and Protein Research, vol. 43, No. 5, Jan. 1, 1994, pp. 477-485.
Legendre JY et al: "Dioleoylmelittin As a Novel Serum-Insensitive Reagent for Efficient Transfection of Mammalian Cells", Bioconjugate Chemistry, vol. 8, No. 1, Jan. 1, 1997, pp. 57-63.
Wolfrum C et al. "Mechanisms and optimization of in vivo delivery of lipophilic siRNAs", Nature Biotechnology, vol. 25, No. 1 0, Oct. 1, 2007, pp. 1149-1157.

* cited by examiner

*Primary Examiner* — Amy Bowman
(74) *Attorney, Agent, or Firm* — Kirk Ekena

(57) ABSTRACT

The present invention is directed compositions for targeted delivery of RNA interference (RNAi) polynucleotides to hepatocytes in vivo. Targeted RNAi polynucleotides are administered together with co-targeted melittin delivery peptides. Delivery peptides provide membrane penetration function for movement of the RNAi polynucleotides from outside the cell to inside the cell. Reversible modification provides physiological responsiveness to the delivery peptides.

14 Claims, 8 Drawing Sheets

FIG. 1. Melittin peptide sequences.

| Seq ID | Melittin Sequence | Name |
|---|---|---|
| 1 | GIGAILKVLATGLPTLISWIKNKRKQ | *Apis florea* |
| 2 | AIGAILKVLATGLPTLISWIKNKRKQ | G1A |
| 3 | CIGAILKVLATGLPTLISWIKNKRKQ | G1C |
| 4 | FIGAILKVLATGLPTLISWIKNKRKQ | G1F |
| 5 | HIGAILKVLATGLPTLISWIKNKRKQ | G1H |
| 6 | IIGAILKVLATGLPTLISWIKNKRKQ | G1I |
| 7 | LIGAILKVLATGLPTLISWIKNKRKQ | G1L |
| 8 | NleIGAILKVLATGLPTLISWIKNKRKQ | G1Nle |
| 9 | VIGAILKVLATGLPTLISWIKNKRKQ | G1V |
| 10 | WIGAILKVLATGLPTLISWIKNKRKQ | G1W |
| 11 | YIGAILKVLATGLPTLISWIKNKRKQ | G1Y |
| 12 | GIGAILKVLACGLPTLISWIKNKRKQ | T11C dMel |
| 13 | GIGAILKVLATLLPTLISWIKNKRKQ | G12L |
| 14 | GIGAILKVLATWLPTLISWIKNKRKQ | G12W |
| 15 | GIGAILKVLATGLPTLISWIKTKRKQ | N22T |
| 16 | YIGAILNVLATGLPTLISWIKNKRKQ | G1Y, K7N |
| 17 | YIGAILAVLATGLPTLISWIKNKRKQ | G1Y, K7A |
| 18 | LIGAILSVLATGLPTLISWIKNKRKQ | G1L, K7S |
| 19 | LIGAILRVLATGLPTLISWIKNKRKQ | G1L, K7R |
| 20 | LIGAILHVLATGLPTLISWIKNKRKQ | G1L, K7H |
| 21 | LIGAILKVLACGLPTLISWIKNKRKQ | G1L, T11C |
| 22 | LIGAILKVLATLLPTLISWIKNKRKQ | G1L, G12L |
| 23 | YIGAILKVLATGLLTLISWIKNKRKQ | G1Y, P14L |
| 24 | LIGAILKVLATGLPCLISWIKNKRKQ | G1L, T15C |
| 25 | LIGAILKVLATGLPTLICWIKNKRKQ | G1L, S18C |
| 26 | YIGAILKVLATGLPTLISAIKNKRKQ | G1Y, W19A |
| 27 | GIGAILKVLACGLPTLISWLKNKRKQ | T11C, I20L |
| 28 | YIGAILKVLATGLPTLISWIANKRKQ | G1Y, K21A |
| 29 | YIGAILKVLATGLPTLISWIKNARKQ | G1Y, K23A |
| 30 | LIGAILKVLATGLPTLISWIKNAKQ | G1L, R24A |
| 31 | YIGAILKVLATGLPTLISWIKNKRAQ | G1Y, K25A |
| 32 | YIGAILKVLATGLPTLISWIKNKRKC | G1Y, Q26C |
| 33 | LLGAILKVLACGLPTLISWIKNKRKQ | G1L, I2L, T11C |
| 34 | LIGALLKVLACGLPTLISWIKNKRKQ | G1L, I5L, T11C |
| 35 | YIGAILAVLATGLPTLISWIANKRKQ | G1Y, K7A, K21A |
| 36 | YIGAILAVLATGLPTLISWIKNARKQ | G1Y, K7A, K23A |
| 37 | LIGAILKVLACGLPTLLSWIKNKRKQ | G1L, T11C, I17L |
| 38 | LIGAILKVLACGlPTLICWIKNKRKQ | G1L, T11C, S18C |
| 39 | GIGAILKVLACGLPGLIGWIKNKRKQ | T11G, T15G, S18G |
| 40 | GIGAILKVLACGLPALIAWIKNKRKQ | T11A, T15A, S18A |
| 41 | YIGAILAVLATGLPTLISWIANARKQ | G1Y, K7A, K21A, K23A |

FIG. 1

| Seq ID | Melittin Sequence | Name |
|---|---|---|
| 42 | YIAAILKVLAAALATLISWIKNKRKQ | G1Y, G3A, T11A, G12A, P14A |
| 43 | LLGALLKVLATGLPTLLSWLKNKRKQ | G1L, I2L, I5L, I17L, I20L |
| 44 | LNleGANleLKVLATGLPTLNleSWNleKNKRKQ | G1L, I2Nle, I5Nle, I17Nle, I20Nle |
| 45 | LVGAVLKVLATGLPTLVSWVKNKRKQ | G1L, I2V, I5V, I17V, I20V |
| 46 | GLGALLKVLACGLPTLLSWLKNKRKQ | I2L, I5L, T11C, I17L, I20L |
| 47 | GNleGANleLKVLACGLPTLNleSWNleKNKRKQ | I2Nle, I5Nle, T11C, I17Nle, I20Nle |
| 48 | CEDDLLLGAILKVLATGLPTLISWIKNKRKQ | CEDDL-Mel G1L, I2L |
| 49 | CLVVLIVVAILKVLATGLPTLISWIKNKRKQ | CLVVL-Mel G1I, I2V, G3V |
| 50 | GIGAVLKVLTTGLPALISWIKRKRQQ | Apis mellifera |
| 51 | CLIGAILKVLATGLPTLISWIKNKRKQ | C-Mel G1L |
| 52 | CNleIGAILKVLATGLPTLISWIKNKRKQ | C-Mel G1Nle |
| 53 | GLIGAILKVLATGLPTLISWIKNKRKQ | G-Mel G1L |
| 54 | LLIGAILKVLATGLPTLISWIKNKRKQ | L-Mel G1L |
| 55 | KLKLIGAILKVLATGLPTLISWIKNKRKQ | KLK-Mel G1L |
| 56 | KLKYIGAILKVLATGLPTLISWIKNKRKQ | KLK-Mel G1Y |
| 57 | CKLKLIGAILKVLATGLPTLISWIKNKRKQ | CKLK-Mel G1L |
| 58 | CKLKNleIGAILKVLATGLPTLISWIKNKRKQ | CKLK-Mel G1Nle |
| 59 | GKLKLIGAILKVLATGLPTLISWIKNKRKQ | GKLK-Mel G1L |
| 60 | CPANLIGAILKVLATGLPTLISWIKNKRKQ | CPAN-dMel G1L |
| 61 | DEPLRAIGAILKVLATGLPTLISWIKNKRKQ | DEPLR-Mel G1A |
| 62 | GIGAILKVLATGLPTLISWIKNKRKQC | Mel-Cys |
| 63 | LIGAILKVLATGLPTLISWIKNKRKQC | G1L Mel-Cys |
| 64 | NleIGAILKVLATGLPTLISWIKNKRKQC | G1Nle Mel-C |
| 65 | LIGAILKVLATGLPTLISWIKNKRKQKLKC | G1L Mel-KLKC |
| 66 | YIGAILKVLATGLPTLISWIKNKRKQPLGIAGQC | G1Y Mel-PLGIAGQC |
| 67 | LIGAILKVLATGLPTLISWIKNKRKQKKKKK | G1L Mel-KKKKK |
| 68 | YIGAILKVLATGLPTLISWIKNKRKQGFKGC | G1Y Mel-GFKGC |
| 69 | CFKLIGAILKVLATGLPTLISWIKNKRKQC | CFK-G1L Mel-C |
| 70 | FGAILKVLATGLPTLISWIKNKRKQ | G1F, I2Δ |
| 71 | LIGAILKVLATGLPTLISWIKNK | G1L Mel (1-23) |
| 72 | LIGAVLKVLTTGLPALISWIK | G1L, L5V, A10T, T15A Mel (1-23) |
| 73 | LIGAVLKVLTTGLPALISWIKGE | G1L, L5V, A10T, T15A, N22G, K23E Mel (1-23) |
| 74 | QKRKNKIWSILTPLGTALVKLIAGIL | G1L retroMel |
| 75 | KLKQKRKNKIWSILTPLGTALVKLIAGIL | G1L retroMel-KLK |
| 76 | GIGAVLKVLTTGLPALISWISRKKRQQ | I5V, A10T, T15A, N22R, R24K, K25R Mel-Q |

FIG. 1 cont.

| Seq ID | Melittin Sequence | Name |
|---|---|---|
| 77 | GIGARLKVLTTGLPRISWIKRKRQQ | I5R, A10T, T15R, L16Δ, N22R, K25Q |
| 78 | GIGAILKVLSTGLPALISWIKRKRQE | A10S, T15A, N22R, K25Q, Q26E |
| 79 | GIGAVLKVLTTGLPALIGWIKRKRQQ | I5V, A10T, T15A, S18G, N22R, K25Q |
| 80 | GIGAVLKVLATGLPALISWIKRKRQQ | I5V, T15A, N22R, K25Q |
| 81 | GIGAVLKVLSTGLPALISWIKRKRQQ | I5V, A10S, T15A, N22R, K25Q |
| 82 | GIGAILRVLATGLPTLISWIKNKRKQ | K7R |
| 83 | GIGAILKVLATGLPTLISWIKRKRKQ | N22R |
| 84 | GIGAILKVLATGLPTLISWIKKKKQQ | N22K, R24K, K25Q |
| 85 | GIGAILKVLATGLPTLISWIKNKRKQGSKKKK | Mel-GSKKKK |
| 86 | KKGIGAILKVLATGLPTLISWIKNKRKQ | KK-Mel |
| 87 | GIGAILEVLATGLPTLISWIKNKRKQ | K7E Mel |
| 88 | GIGAVLKVLTTGLPALISWIKRKR | I5V, T15A, N22R, 25-26Δ |
| 89 | GIGAVLKVLTTGLPALISWIKR | I5V, T15A, N22R, 23-26Δ |
| 90 | CIGAVLKVLTTGLPALISWIKRKRQQ | G1C, I5L, T15A, N22R |
| 91 | QQRKRKIWSILAPLGTTLVKLVAGIG | I5V, A10T, T15A, N22R retroMel |
| 92 | QQRKRKIWSILAPLGTTLVKLVAGIC | G1C, I5V, A10T, T15A, N22R retroMel |
| 93 | QQKKKKIWSILAPLGTTLVKLVAGIC | G1C, I5V, A10T, T15A, N22R, R24K retroMel |
| 94 | QKRKNKIWSILTPLGTALVKLIAGIG | Q25K reverse Mel |
| 95 | QQRKRKIWSILAALGTTLVKLVAGIC | G1C, I5V, A10T, P14A, T15A, N22R retroMel | dMel = Melittin peptide having D-form amino acids

FIG. 1 cont.

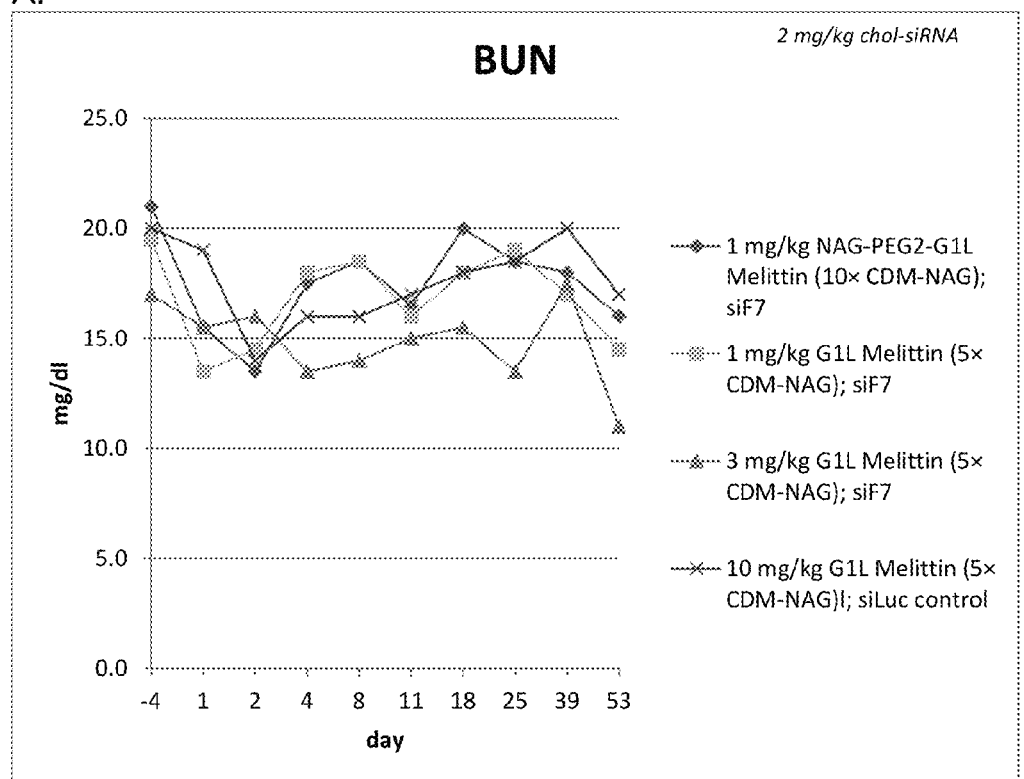
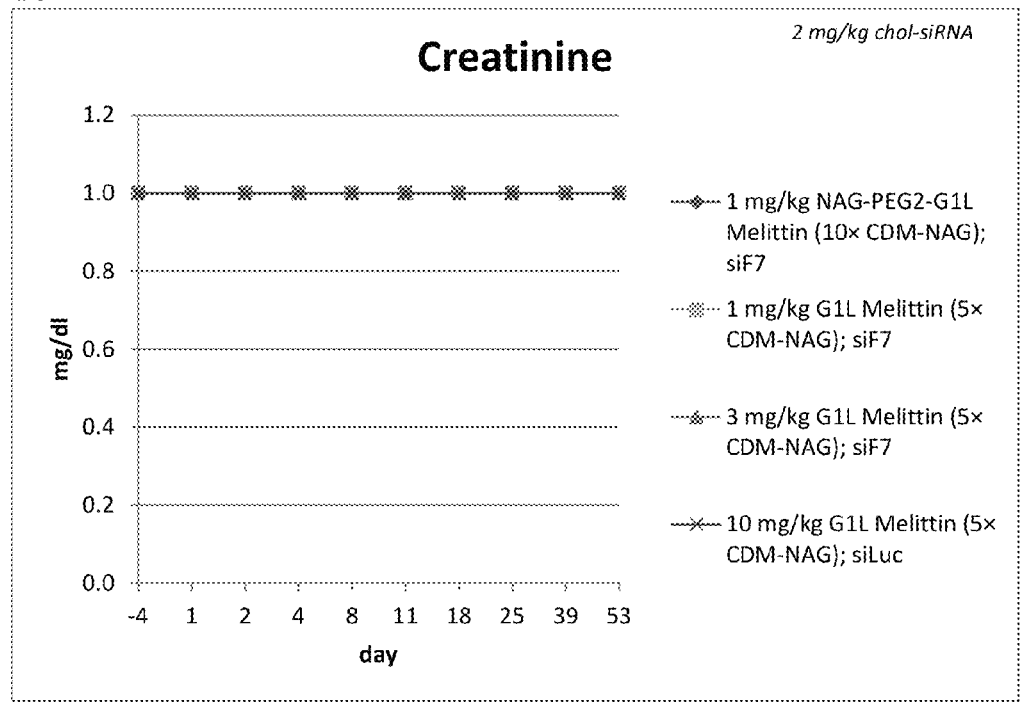
FIG. 3

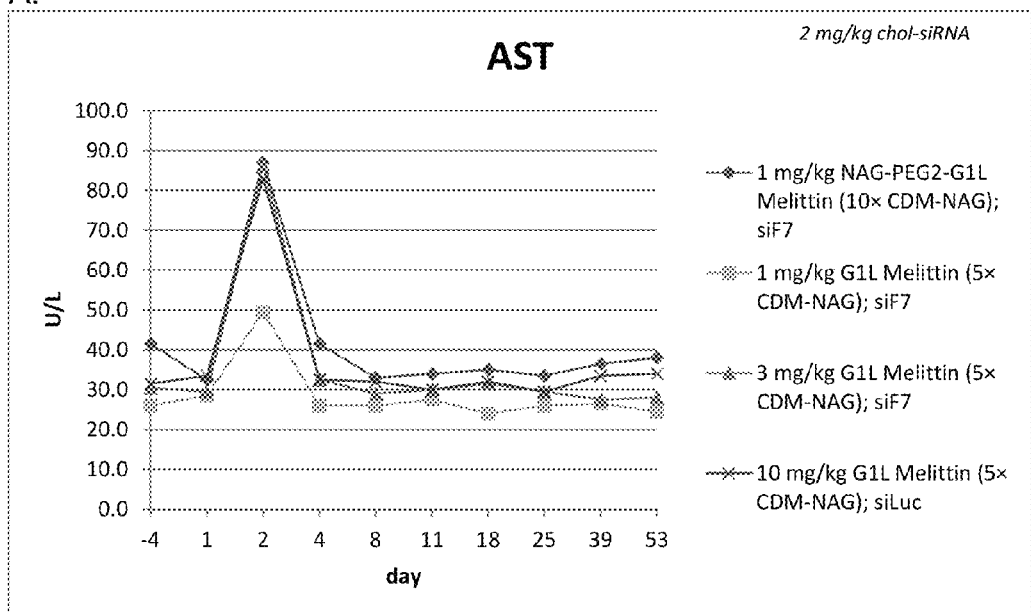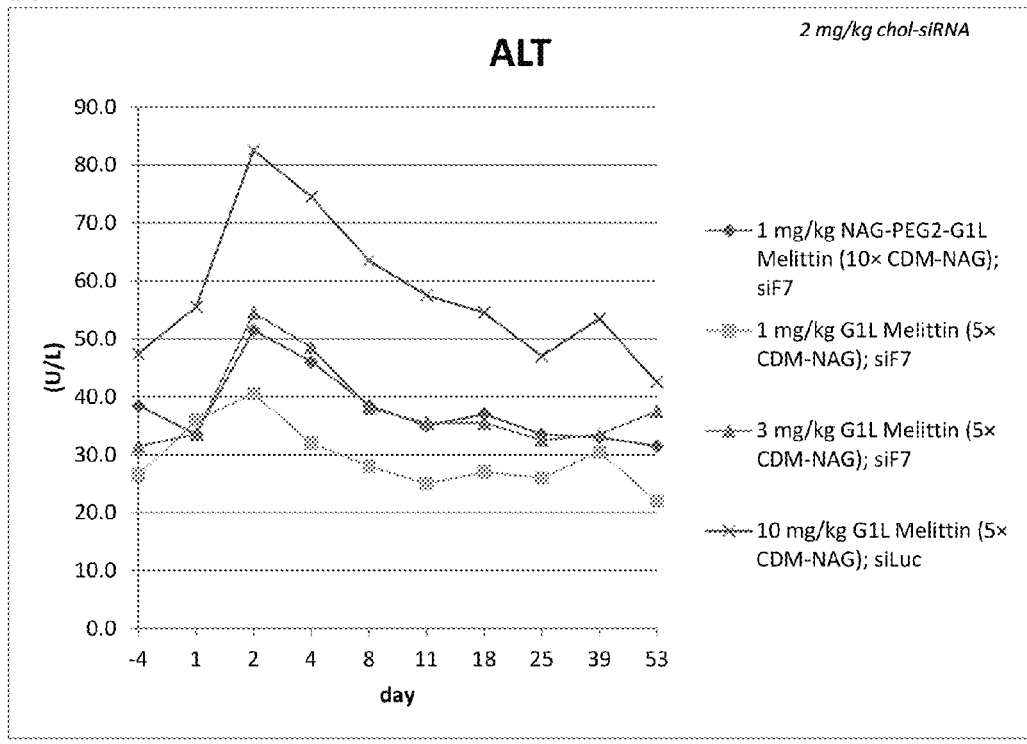
FIG. 4

PEPTIDE-BASED IN VIVO SIRNA DELIVERY SYSTEM

CROSS-REFERENCE TO RELATED APPLICATIONS

This application is a continuation of U.S. Ser. No. 13/326,433, 15 Dec. 2011, which claims the benefit of U.S. Provisional Application No. 61/424,191, filed 17 Dec. 2010.

BACKGROUND OF THE INVENTION

The delivery of polynucleotide and other substantially cell membrane impermeable compounds into a living cell is highly restricted by the complex membrane system of the cell. Drugs used in antisense, RNAi, and gene therapies are relatively large hydrophilic polymers and are frequently highly negatively charged. Both of these physical characteristics severely restrict their direct diffusion across the cell membrane. For this reason, the major barrier to polynucleotide delivery is the delivery of the polynucleotide across a cell membrane to the cell cytoplasm or nucleus.

One means that has been used to deliver small nucleic acid in vivo has been to attach the nucleic acid to either a small targeting molecule or a lipid or sterol. While some delivery and activity has been observed with these conjugates, the very large nucleic acid dose required with these methods is impractical.

Numerous transfection reagents have also been developed that achieve reasonably efficient delivery of polynucleotides to cells in vitro. However, in vivo delivery of polynucleotides using these same transfection reagents is complicated and rendered ineffective by in vivo toxicity, adverse serum interactions, or poor targeting. Transfection reagents that work well in vitro, cationic polymers and lipids, typically form large cationic electrostatic particles and destabilize cell membranes. The positive charge of in vitro transfection reagents facilitates association with nucleic acid via charge-charge (electrostatic) interactions thus forming the nucleic acid/transfection reagent complex. Positive charge is also beneficial for nonspecific binding of the vehicle to the cell and for membrane fusion, destabilization, or disruption. Destabilization of membranes facilitates delivery of the substantially cell membrane impermeable polynucleotide across a cell membrane. While these properties facilitate nucleic acid transfer in vitro, they cause toxicity and ineffective targeting in vivo. Cationic charge results in interaction with serum components, which causes destabilization of the polynucleotide-transfection reagent interaction, poor bioavailability, and poor targeting. Membrane activity of transfection reagents, which can be effective in vitro, often leads to toxicity in vivo.

For in vivo delivery, the vehicle (nucleic acid and associated delivery agent) should be small, less than 100 nm in diameter, and preferably less than 50 nm. Even smaller complexes, less that 20 nm or less than 10 nm would be more useful yet. Delivery vehicles larger than 100 nm have very little access to cells other than blood vessel cells in vivo. Complexes formed by electrostatic interactions tend to aggregate or fall apart when exposed to physiological salt concentrations or serum components. Further, cationic charge on in vivo delivery vehicles leads to adverse serum interactions and therefore poor bioavailability. Interestingly, high negative charge can also inhibit targeted in vivo delivery by interfering with interactions necessary for targeting, i.e. binding of targeting ligands to cellular receptors. Thus, near neutral vehicles are desired for in vivo distribution and targeting. Without careful regulation, membrane disruption or destabilization activities are toxic when used in vivo. Balancing vehicle toxicity with nucleic acid delivery is more easily attained in vitro than in vivo.

Rozema et al., in U.S. Patent Publication 20040162260 demonstrated a means to reversibly regulate membrane disruptive activity of a membrane active polyamine. The membrane active polyamine provided a means of disrupting cell membranes. pH-dependent reversible regulation provided a means to limit activity to the endosomes of target cells, thus limiting toxicity. Their method relied on modification of amines on a polyamine with 2-propionic-3-methylmaleic anhydride.

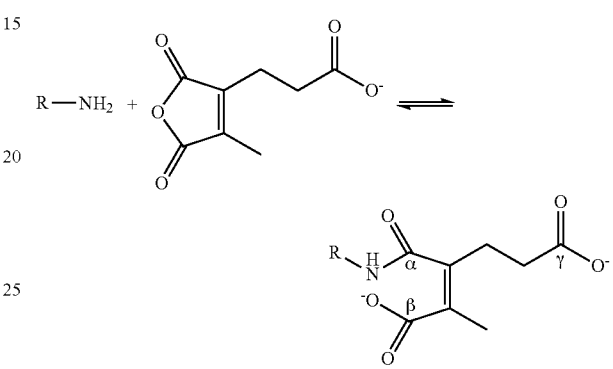

This modification converted the polycation to a polyanion via conversion of primary amines to pairs of carboxyl groups (β carboxyl and γ carboxyl) and reversibly inhibited membrane activity of the polyamine. Rozema et al. (Bioconjugate Chem. 2003, 14, 51-57) reported that the β carboxyl did not exhibit a full apparent negative charge and by itself was not able to inhibit membrane activity. The addition of the γ carboxyl group was reported to be necessary for effective membrane activity inhibition. To enable co-delivery of the nucleic acid with the delivery vehicle, the nucleic acid was covalently linked to the delivery polymer. They were able to show delivery of polynucleotides to cells in vitro using their biologically labile conjugate delivery system. However, because the vehicle was highly negatively charged, with both the nucleic acid and the modified polymer having high negative charge density, this system was not efficient for in vivo delivery. The negative charge likely inhibited cell-specific targeting and enhanced non-specific uptake by the reticuloentothelial system (RES).

Rozema et al., in U.S. Patent Publication 20080152661, improved on the method of U.S. Patent Publication 20040162260 by eliminating the high negative charge density of the modified membrane active polymer. By substituting neutral hydrophilic targeting (galactose) and steric stabilizing (PEG) groups for the γ carboxyl of 2-propionic-3-methylmaleic anhydride, Rozema et al. were able to retain overall water solubility and reversible inhibition of membrane activity while incorporating effective in vivo hepatocyte cell targeting. As before, the polynucleotide was covalently linked to the transfection polymer. Covalent attachment of the polynucleotide to the transfection polymer was maintained to ensure co-delivery of the polynucleotide with the transfection polymer to the target cell during in vivo administration by preventing dissociation of the polynucleotide from the transfection polymer. Co-delivery of the polynucleotide and transfection polymer was required because the transfection polymer provided for transport of the polynucleotide across a cell membrane, either from outside the cell or from inside an endocytic compartment, to the cell cytoplasm. U.S. Patent Publication 20080152661 demonstrated highly efficient delivery of polynucleotides, specifically RNAi oligonucleotides, to liver cells in vivo using this new improved physiologically responsive polyconjugate.

However, covalent attachment of the nucleic acid to the polyamine carried inherent limitations. Modification of the transfection polymers, to attach both the nucleic acid and the masking agents was complicated by charge interactions. Attachment of a negatively charged nucleic acid to a positively charged polymer is prone to aggregation thereby limiting the concentration of the mixture. Aggregation could be overcome by the presence of an excess of the polycation or polyanion. However, this solution limited the ratios at which the nucleic acid and the polymer may be formulated. Also, attachment of the negatively charged nucleic acid onto the unmodified cationic polymer caused condensation and aggregation of the complex and inhibited polymer modification. Modification of the polymer, forming a negative polymer, impaired attachment of the nucleic acid.

Rozema et al. further improved upon the technology described in U.S. Patent Publication 20080152661, in U.S. Provisional Application 61/307,490. In U.S. Provisional Application 61/307,490, Rozema et al. demonstrated that, by carefully selecting targeting molecules, and attaching appropriate targeting molecules independently to both an siRNA and a delivery polymer, the siRNA and the delivery polymer could be uncoupled yet retain effective targeting of both elements to cells in vivo and achieve efficient functional targeted delivery of the siRNA. The delivery polymers used in both U.S. Patent Publication 20080152661 and U.S. Provisional Application 61/307,490 were relatively large synthetic polymers, poly(vinyl ether)s and poly(acrylate)s. The larger polymers enabled modification with both targeting ligands for cell-specific binding and PEG for increased shielding. Larger polymers were necessary for effective delivery, possibly through increased membrane activity and improved protection of the nucleic acid within the cell endosome. Larger polycations interact more strongly with both membranes and with anionic RNAs.

We have now developed an improved siRNA delivery system using a much smaller delivery peptide. The improved system provides for efficient siRNA delivery with decreased toxicity and therefore a wider therapeutic window.

SUMMARY OF THE INVENTION

In a preferred embodiment, the invention features a composition for delivering an RNA interference polynucleotide to a liver cell in vivo comprising: a) an asialoglycoprotein receptor (ASGPr)-targeted reversibly masked melittin peptide (delivery peptide) and b) an RNA interference polynucleotide conjugated to a hydrophobic group containing at least 20 carbon atoms (RNA-conjugate). The delivery peptide and the siRNA-conjugate are synthesized separately and may be supplied in separate containers or a single container. The RNA interference polynucleotide is not conjugated to the delivery peptide.

In another preferred embodiment, the invention features a composition for delivering an RNA interference polynucleotide to a liver cell in vivo comprising: a) an ASGPr-targeted reversibly masked melittin peptide (delivery peptide) and b) an RNA interference polynucleotide conjugated to a galactose cluster (RNA conjugate). The delivery peptide and the siRNA-conjugate are synthesized separately and may be supplied in separate containers or a single container. The RNA interference polynucleotide is not conjugated to the polymer.

In a preferred embodiment, an ASGPr-targeted reversibly masked melittin peptide comprises a melittin peptide reversibly modified by reaction of primary amines on the peptide with ASGPr ligand-containing masking agents. An amine is reversibly modified if cleavage of the modifying group restores the amine. Reversible modification of the melittin peptide with the masking agents disclosed herein reversibly inhibits membrane activity of the melittin peptide. In the masked state, the reversibly masked melittin peptide does not exhibit membrane disruptive activity. Reversible modification of more than 80%, or more than 90%, of the amines on the melittin peptide is required to inhibit membrane activity and provide cell targeting function, i.e. form a reversibly masked melittin peptide.

A preferred ASGPr ligand-containing masking agent has a neutral charge and comprises a galactosamine or galactosamine derivative having a disubstituted maleic anhydride amine-reactive group. Another preferred ASGPr ligand-containing masking agent comprises a galactosamine or galactosamine derivative having a peptidase cleavable dipeptide-p-amidobenzyl amine reactive carbonate derivative. Reaction of the amine reactive carbonate with an amine reversibly modifies the amine to form an amidobenzyl carbamate linkage.

In a preferred embodiment, a melittin peptide comprises an *Apis florea* (little or dwarf honey bee) melittin, *Apis mellifera* (western or European or big honey bee), *Apis dorsata* (giant honey bee), *Apis cerana* (oriental honey bee) or derivatives thereof. A preferred melittin peptide comprises the sequence: $Xaa_1$-$Xaa_2$-$Xaa_3$-Ala-$Xaa_5$-Leu-$Xaa_7$-Val-Leu-$Xaa_{10}$-$Xaa_{11}$-$Xaa_{12}$-Leu-Pro-$Xaa_{15}$-Leu-$Xaa_{17}$-$Xaa_{18}$-Trp-$Xaa_{20}$-$Xaa_{21}$-$Xaa_{22}$-$Xaa_{23}$-$Xaa_{24}$-$Xaa_{25}$-$Xaa_{26}$ wherein:

$Xaa_1$ is leucine, D-leucine, isoleucine, norleucine, tyrosine, tryptophan, valine, alanine, dimethylglycine, glycine, histidine, phenylalanine, or cysteine,
$Xaa_2$ is isoleucine, leucine, norleucine, or valine,
$Xaa_3$ is glycine, leucine, or valine,
$Xaa_5$ is isoleucine, leucine, norleucine, or valine,
$Xaa_7$ is lysine, serine, asparagine, alanine, arginine, or histidine,
$Xaa_{10}$ is alanine, threonine, or leucine,
$Xaa_{11}$ is threonine or cysteine,
$Xaa_{12}$ is glycine, leucine, or tryptophan,
$Xaa_{15}$ is threonine or alanine,
$Xaa_{17}$ is isoleucine, leucine, norleucine, or valine,
$Xaa_{18}$ is serine or cysteine,
$Xaa_{20}$ is isoleucine, leucine, norleucine, or valine,
$Xaa_{21}$ is lysine or alanine,
$Xaa_{22}$ is asparagine or arginine,
$Xaa_{23}$ is lysine or alanine,
$Xaa_{24}$ is arginine or lysine,
$Xaa_{25}$ is lysine, alanine, or glutamine,
$Xaa_{26}$ is optional and if present is glutamine, cysteine, glutamine-$NH_2$, or cysteine-$NH_2$; and,
and at least two of $Xaa_{21}$, $Xaa_{23}$, and $Xaa_{25}$ are lysine.

A more preferred melittin comprises the sequence: $Xaa_1$-$Xaa_2$-$Xaa_3$-Ala-$Xaa_5$-Leu-$Xaa_7$-Val-Leu-$Xaa_{10}$-$Xaa_{11}$-$Xaa_{12}$-Leu-Pro-$Xaa_{15}$-Leu-$Xaa_{17}$-Ser-Trp-$Xaa_{20}$-Lys-$Xaa_{22}$-Lys-Arg-Lys-$Xaa_{26}$ wherein:

$Xaa_1$ is leucine, D-leucine, norleucine, or tyrosine,
$Xaa_2$ is isoleucine, leucine, norleucine, or valine,
$Xaa_3$ is glycine, leucine, or valine,
$Xaa_5$ is isoleucine, valine, leucine, or norleucine,
$Xaa_7$ is lysine, serine, asparagine, alanine, arginine, or histidine,
$Xaa_{10}$ is alanine, threonine, or leucine,
$Xaa_{11}$ is threonine, or cysteine, $Xaa_{12}$ is glycine, leucine, or tryptophan,
$Xaa_{15}$ is threonine, or alanine,
$Xaa_{17}$ is isoleucine, leucine, or norleucine,
$Xaa_{20}$ is isoleucine, leucine, or norleucine,
$Xaa_{22}$ is asparagine or arginine, and
$Xaa_{26}$ is glutamine or cysteine.

A most preferred melittin comprises the sequence: $Xaa_1$-$Xaa_2$-Gly-Ala-$Xaa_5$-Leu-Lys-Val-Leu-Ala-$Xaa_{11}$-Gly-Leu-Pro-Thr-Leu-$Xaa_{17}$-Ser-Trp-$Xaa_{20}$-Lys-$Xaa_{22}$-Lys-Arg-Lys-$Xaa_{26}$ wherein:

$Xaa_1$, $Xaa_2$, $Xaa_5$, $Xaa_{17}$ and $Xaa_{20}$ are independently isoleucine, leucine, or norleucine,
$Xaa_{11}$ is threonine or cysteine,
$Xaa_{22}$ is Asparagine or arginine, and
$Xaa_{26}$ is glutamine or cysteine.

A preferred masking agent comprises a neutral hydrophilic disubstituted alkylmaleic anhydride:

wherein R1 comprises a cell targeting group. A preferred alkyl group is a methyl or ethyl group. A preferred targeting group comprises an asialoglycoprotein receptor ligand. An example of a substituted alkylmaleic anhydride consists of a 2-propionic-3-alkylmaleic anhydride derivative. A neutral hydrophilic 2-propionic-3-alkylmaleic anhydride derivative is formed by attachment of a neutral hydrophilic group to a 2-propionic-3-alkylmaleic anhydride through the 2-propionic-3-alkylmaleic anhydride γ-carboxyl group:

wherein R1 comprises a neutral ASGPr ligand and n=0 or 1. In one embodiment, the ASGPr ligand is linked to the anhydride via a short PEG linker.

A preferred masking agent comprises a hydrophilic peptidase (protease) cleavable dipeptide-p-amidobenzyl amine reactive carbonate derivative. Enzyme cleavable linkers of the invention employ a dipeptide connected to an amidobenzyl activated carbonate moiety. The ASGPr ligand is attached to the amino terminus of a dipeptide. The amidobenzyl activated carbonate moiety is at the carboxy terminus of the dipeptide. Peptidease cleavable linkers suitable for use with the invention have the structure:

wherein R4 comprises an ASGPr ligand and R3 comprises an amine reactive carbonate moiety, and R1 and R2 are amino acid R groups. A preferred activated carbonate is a paranitrophenol. However, other amine reactive carbonates known in the art are readily substituted for the para-nitrophenol. Reaction of the activated carbonate with a melittin amine connects the targeting compound, the asialoglycoprotein receptor ligand, to the melittin peptide via a peptidase cleavable dipeptide-amidobenzyl carbamate linkage. Enzyme cleavage of the dipeptide removes the targeting ligand from the peptide and triggers an elimination reaction which results in regeneration of the peptide amine.

Dipeptides Glu-Gly, Ala-Cit, Phe-Cit ("Cit" is the amino acid citrulline) are shown in Example 3. While charged amino acids also permissible, neutral amino acids are preferred.

A preferred masking agent provides targeting function through affinity for cell surface receptors, i.e. the masking agent contains a ligand for a cell surface receptor. Preferred masking agents contain saccharides having affinity for the ASGPr, including but not limited to: galactose, N-Acetyl-galactosamine and galactose derivatives. Galactose derivatives having affinity for the ASGPr are well known in the art. An essential feature of the reversibly modified melittin is that more than 80% of the melittin amines (in a population of peptide) are modified by attachment of ASGPr ligands via physiologically labile, reversible covalent linkages.

In another embodiment, the melittin peptides of the invention are further modified, at the amino or carboxyl termini, by covalent attachment of a steric stabilizer or an ASGPr ligand-steric stabilizer conjugate. The amino or carboxy terminal modifications may be linked to the peptide during synthesis using methods standard in the art. Alternatively, the amino or carboxy terminal modifications may be done through modification of cysteine residues on melittin peptide having amino or carboxy terminal cysteine residues. A preferred steric stabilizer is a polyethylene glycol. Preferred polyethylene glycols have 1-120 ethylene units. In another embodiment, preferred polyethylene glycols are less than 5 kDa in size. For ASGPr ligand-steric stabilizer conjugates, a preferred steric stabilizer is a polyethyleneglycol having 1-24 ethylene units.

The RNAi polynucleotide conjugate and delivery peptide are administered to a mammal in pharmaceutically acceptable carriers or diluents. In one embodiment, the delivery peptide and the RNAi polynucleotide conjugate may be combined in a solution prior to administration to the mammal. In another embodiment, the delivery peptide and the RNAi polynucleotide conjugate may be co-administered to the mammal in separate solutions. In yet another embodiment, the delivery peptide and the RNAi polynucleotide conjugate may be administered to the mammal sequentially. For sequential administration, the delivery peptide may be administered prior to administration of the RNAi polynucleotide conjugate. Alternatively, for sequential administration, the RNAi polynucleotide conjugate may be administered prior to administration of the delivery peptide.

Further objects, features, and advantages of the invention will be apparent from the following detailed description when taken in conjunction with the accompanying drawings.

BRIEF DESCRIPTION OF THE FIGURES

FIG. 1 Table listing melittin peptides suitable for use in the invention.
FIG. 3. Graph illustrating (A) blood urea nitrogen (BUN) levels and (B) creatinine levels in primates treated with reversibly modified melittin siRNA delivery peptides and siRNA-cholesterol conjugates.

FIG. 4. Graph illustrating (A) aspartate aminotransferase (AST) levels and (B) alanine transaminase (ALT) levels in primates treated with reversibly modified melittin siRNA delivery peptides and siRNA-cholesterol conjugates.

DETAILED DESCRIPTION OF THE INVENTION

Figure 2:
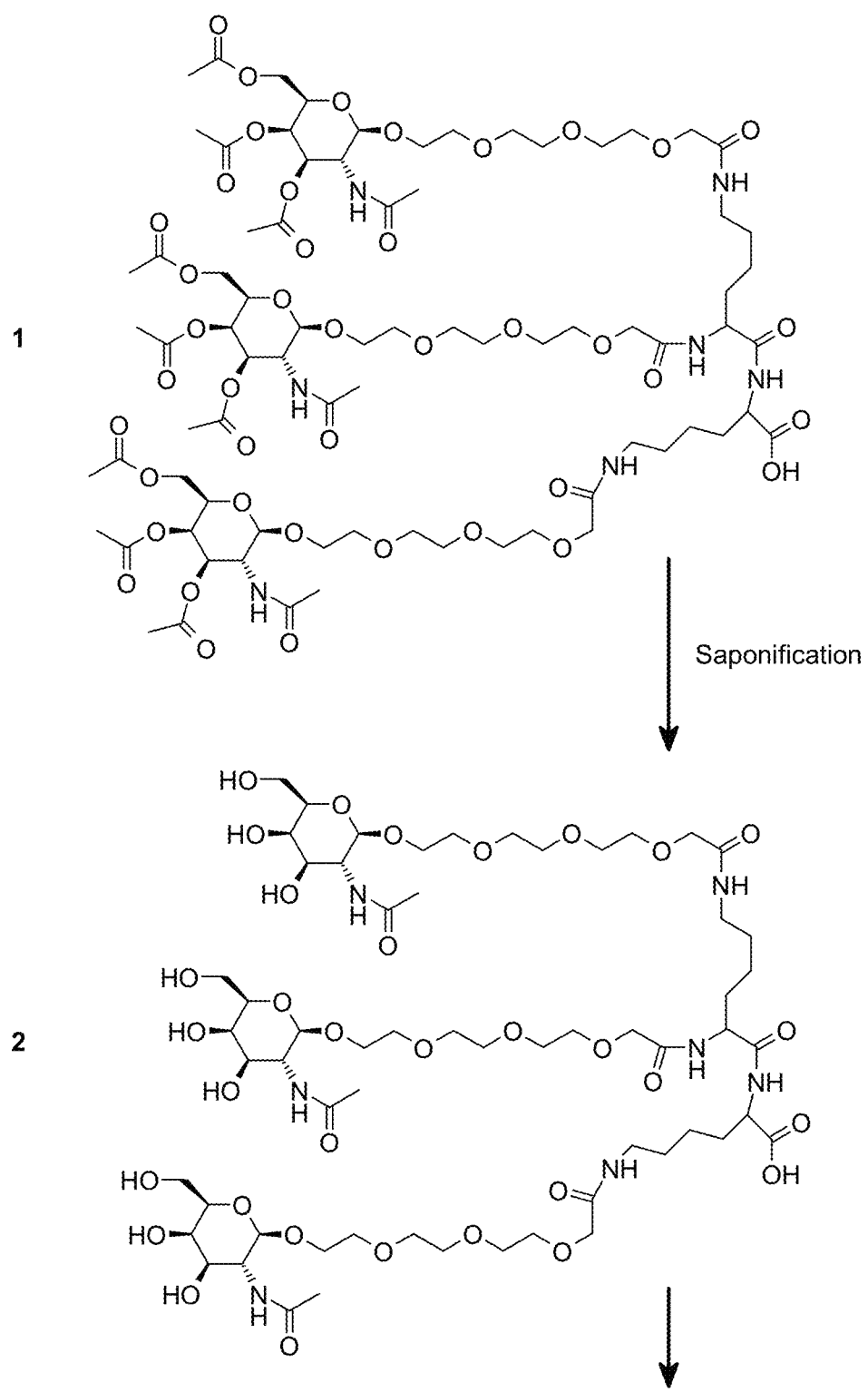
FIG. 2. Drawing illustrating linkage of GalNAc cluster to RNA.
Figure 2:
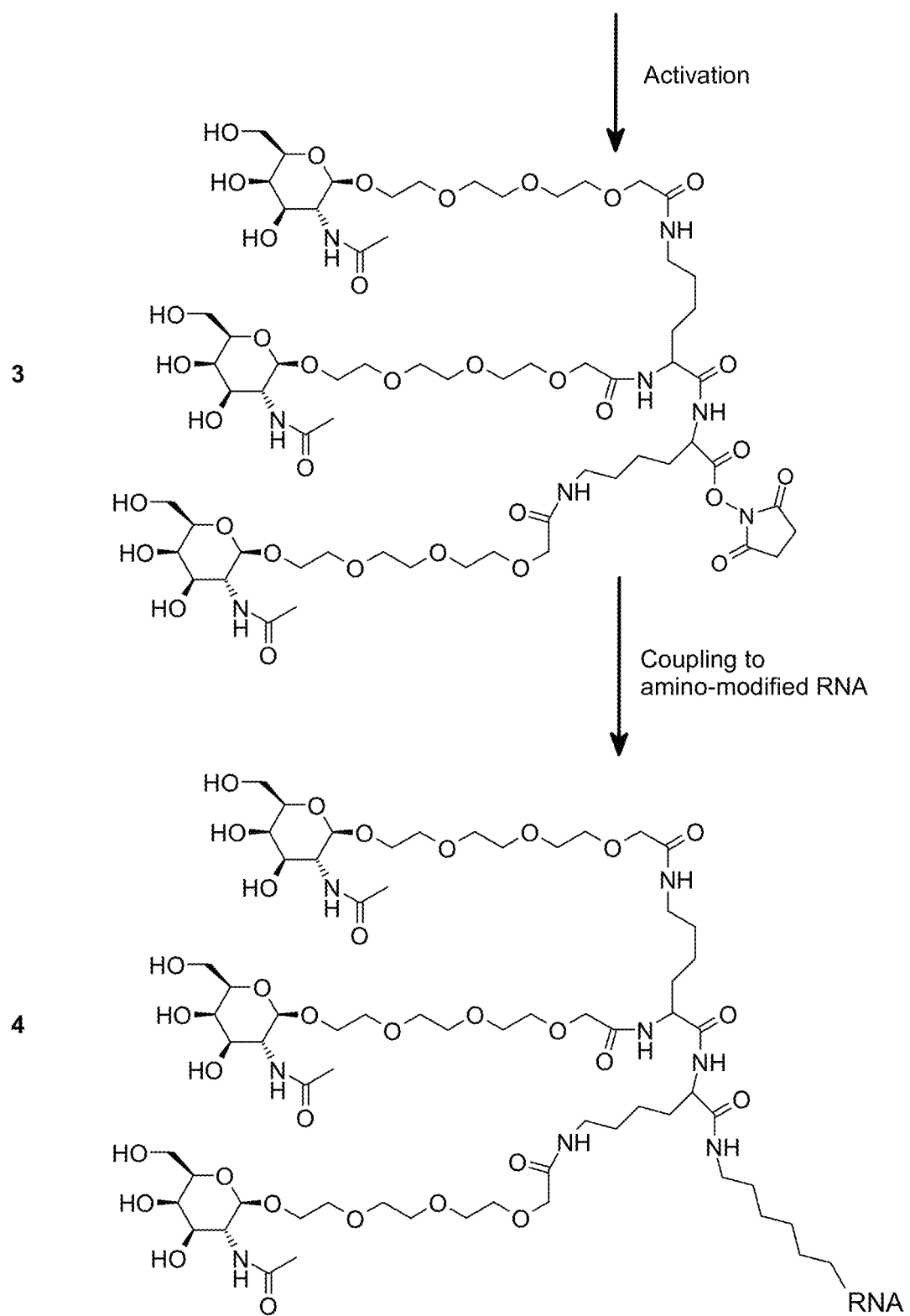

Described herein is an improved method for delivering RNA interference (RNAi) polynucleotides to liver cells in a mammal in vivo. We describe an in vivo RNAi polynucleotide delivery system employing a small delivery peptide, melittin, derived from bee venom peptide and an independently targeting RNAi polynucleotide. By using liver targeted RNAi polynucleotide conjugate molecules and asialoglycoprotein receptor targeted reversibly inhibited melittin peptides, efficient RNAi polynucleotide delivery to liver is observed.

Because the melittin and RNAi polynucleotide are independently targeted to hepatocytes, the concentration of the melittin and polynucleotides and the ratio between them is limited only by the solubility of the components rather than the solubility of the associated complex or ability to manufacture the complex. Also, the polynucleotide and melittin may be mixed at anytime prior to administration, or even administered separately, thus allowing the components to be stored separately, either in solution or dry.

The invention includes conjugate delivery systems of the composition:

Y-Melittin-(L-M)$_x$ plus N-T, wherein N is a RNAi polynucleotide, T is a polynucleotide targeting moiety (either a hydrophobic group having 20 or more carbon atoms or a galactose cluster), Melittin is a bee venom melittin peptide or a derivative as describe herein, and masking agent M contains an ASGPr ligand as described herein covalently linked to Melittin via a physiologically labile reversible linkage L. Cleavage of L restores an unmodified amine on Melittin. Y is optional and if present comprises a polyethyleneglycol (PEG) or a ASGPr ligand-PEG conjugate linked to the amino terminus, the carboxy terminus, or an amino or carboxy terminal cysteine of Melittin. Attachment of Y to the amino terminus or an amino terminal cysteine is preferred. x is an integer greater than 1. In its unmodified state, Melittin is membrane active. However, delivery peptide Melittin-(L-M)$_x$ is not membrane active. Reversible modification of Melittin primary amines, by attachment of M reversibly inhibits or inactivates membrane activity of Melittin. Sufficient percentage of Melittin primary amines are modified to inhibit membrane activity of the polymer and provide for hepatocyte targeting. Preferably x has a value greater than 80%, and more preferably greater than 90%, of the primary amines on Melittin, as determined by the quantity of amines on Melittin in the absence of any masking agents. More specifically, x has a value greater than 80% and up to 100% of the primary amines on Melittin. It is noted that melittin typically contains 3-5 primary amines (the amino terminus (if unmodified) and typically 2-4 Lysine residues). Therefore, modification of a percentage of amines is meant to reflect the modification of a percentage on amines in a population of melittin peptides. Upon cleavage of reversible linkages L, unmodified amines are restored thereby reverting Melittin to its unmodified, membrane active state. A preferred reversible linkage is a pH labile linkage. Another preferred reversible linkage is a protease cleavable linkage. Melittin-(L-M)$_x$, an ASGPr-targeted reversibly masked membrane active polymer (delivery peptide), and T-N, a polynucleotide-conjugate, are synthesized or manufactured separately. Neither T nor N are covalently linked directly or indirectly to Melittin, L, or M. Electrostatic or hydrophobic association of the polynucleotide or the polynucleotide-conjugate with the masked or unmasked polymer is not required for in vivo liver delivery of the polynucleotide. The masked polymer and the polynucleotide conjugate can be supplied in the same container or in separate containers. They may be combined prior to administration, co-administered, or administered sequentially.

Hydrophilic groups indicate in qualitative terms that the chemical moiety is water-preferring. Typically, such chemical groups are water soluble, and are hydrogen bond donors or acceptors with water. A hydrophilic group can be charged or uncharged. Charged groups can be positively charged (anionic) or negatively charged (cationic) or both (zwitterionic). Examples of hydrophilic groups include the following chemical moieties: carbohydrates, polyoxyethylene, certain peptides, oligonucleotides, amines, amides, alkoxy amides, carboxylic acids, sulfurs, and hydroxyls.

Hydrophobic groups indicate in qualitative terms that the chemical moiety is water-avoiding. Typically, such chemical groups are not water soluble, and tend not to form hydrogen bonds. Lipophilic groups dissolve in fats, oils, lipids, and non-polar solvents and have little to no capacity to form hydrogen bonds. Hydrocarbons containing two (2) or more carbon atoms, certain substituted hydrocarbons, cholesterol, and cholesterol derivatives are examples of hydrophobic groups and compounds.

Hydrophobic groups are preferably hydrocarbons, containing only carbon and hydrogen atoms. However, non-polar substitutions or non-polar heteroatoms which maintain hydrophobicity, and include, for example fluorine, may be permitted. The term includes aliphatic groups, aromatic groups, acyl groups, alkyl groups, alkenyl groups, alkynyl groups, aryl groups, aralkyl groups, aralkenyl groups, and aralkynyl groups, each of which may be linear, branched, or cyclic. The term hydrophobic group also includes: sterols, steroids, cholesterol, and steroid and cholesterol derivatives.

As used herein, membrane active peptides are surface active, amphipathic peptides that are able to induce one or more of the following effects upon a biological membrane: an alteration or disruption of the membrane that allows non-membrane permeable molecules to enter a cell or cross the membrane, pore formation in the membrane, fission of membranes, or disruption or dissolving of the membrane. As used herein, a membrane, or cell membrane, comprises a lipid bilayer. The alteration or disruption of the membrane can be functionally defined by the peptide's activity in at least one the following assays: red blood cell lysis (hemolysis), liposome leakage, liposome fusion, cell fusion, cell lysis, and endosomal release. Membrane active peptides that can cause lysis of cell membranes are also termed membrane lytic peptides. Peptides that preferentially cause disruption of endosomes or lysosomes over plasma membranes are considered endosomolytic. The effect of membrane active peptides on a cell membrane may be transient. Membrane active peptides possess affinity for the membrane and cause a denaturation or deformation of bilayer structures.

Delivery of a polynucleotide to a cell is mediated by the melittin peptide disrupting or destabilizing the plasma membrane or an internal vesicle membrane (such as an endosome or lysosome), including forming a pore in the membrane, or disrupting endosomal or lysosomal vesicles thereby permitting release of the contents of the vesicle into the cell cytoplasm.

Endosomolytic peptides are peptides that, in response to an endosomal-specific environmental factors, such as reduced pH or the presence of lytic enzymes (proteases), are able to cause disruption or lysis of an endosome or provide for release of a normally cell membrane impermeable compound, such as a polynucleotide or protein, from a cellular internal membrane-enclosed vesicle, such as an endosome or lysosome. Endosomolytic polymers undergo a shift in their physico-chemical properties in the endosome. This shift can be a change in the polymer's solubility or ability to interact with other compounds or membranes as a result in a shift in charge, hydrophobicity, or hydrophilicity. Exemplary endosomolytic peptides have pH-labile or enzymatic-sensitive groups or bonds. A reversibly masked membrane active peptide, wherein the masking agents are attached to the polymer via pH labile bonds, can therefore be considered to be an endosomolytic polymer.

Melittin, as used herein, is a small amphipathic membrane active peptide, comprising about 23 to about 32 amino acids, derived from the naturally occurring in bee venom peptide melittin. The naturally occurring melittin contains 26 amino acids and is predominantly hydrophobic on the amino terminal end and predominantly hydrophilic (cationic) on the carboxy terminal end. Melittin of the invention can be isolated from a biological source or it can be synthetic. A synthetic polymer is formulated or manufactured by a chemical process "by man" and is not created by a naturally occurring biological process. As used herein, melittin encompasses the naturally occurring bee venom peptides of the melittin family that can be found in, for example, venom of the species: *Apis florea, Apis mellifera, Apis cerana, Apis dorsata, Vespula maculifrons, Vespa magnifica, Vespa velutina, Polistes* sp. HQL-2001, and *Polistes hebraeus*. As used herein, melittin also encompasses synthetic peptides having amino acid sequence identical to or similar to naturally occurring melittin peptides. Specifically, melittin amino acid sequence encompass those shown in FIG. 1. In addition to the amino acids which retain melittin's inherent high membrane activity, 1-8 amino acids can be added to the amino or carboxy terminal ends of the peptide. Specifically, cysteine residues can be added to the amino or carboxy termini. The list in FIG. 1 is not meant to be exhaustive, as other conservative amino acid substitutions are readily envisioned. Synthetic melittin peptides can contain naturally occurring L form amino acids or the enantiomeric D form amino acids (inverso). However, a melittin peptide should either contain essentially all L form or all D form amino acids but may have amino acids of the opposite stereocenter appended at either the amino or carboxy termini. The melittin amino acid sequence can also be reversed (retro). Retro melittin can have L form amino acids or D form amino acids (retroinverso). Two melittin peptides can also be covalently linked to form a melittin dimer. Melittin can have modifying groups, other that masking agents, that enhance tissue targeting or facilitate in vivo circulation attached to either the amino terminal or carboxy terminal ends of the peptide. However, as used herein, melittin does not include chains or polymers containing more than two melittin peptides covalently linked to one another other or to another polymer or scaffold.

Masking

The melittin peptides of the invention comprise reversibly modified melittin peptides wherein reversible modification inhibits membrane activity, neutralizes the melittin to reduce positive charge and form a near neutral charge polymer, and provides cell-type specific targeting. The melittin is reversibly modified through reversible modification of primary amines on the peptide.

The melittin peptides of the invention are capable of disrupting plasma membranes or lysosomal/endocytic membranes. Membrane activity, however, leads to toxicity when the peptide is administered in vivo. Therefore, reversible masking of membrane activity of melittin is necessary for in vivo use. This masking is accomplished through reversible attachment of masking agents to melittin to form a reversibly masked melittin, i.e. a delivery peptide. In addition to inhibiting membrane activity, the masking agents provide cell-specific interactions, i.e. targeting.

It is an essential feature of the masking agents that, in aggregate, they inhibit membrane activity of the polymer and provide in vivo hepatocyte targeting. Melittin is membrane active in the unmodified (unmasked) state and not membrane active (inactivated) in the modified (masked) state. A sufficient number of masking agents are linked to the peptide to achieve the desired level of inactivation. The desired level of modification of melittin by attachment of masking agent(s) is readily determined using appropriate peptide activity assays. For example, if melittin possesses membrane activity in a given assay, a sufficient level of masking agent is linked to the peptide to achieve the desired level of inhibition of membrane activity in that assay. Modification of ≥80% or ≥90% of the primary amine groups on a population of melittin peptides, as determined by the quantity of primary amines on the peptides in the absence of any masking agents, is preferred. It is also a preferred characteristic of masking agents that their attachment to the peptide reduces positive charge of the polymer, thus forming a more neutral delivery peptide. It is desirable that the masked peptide retain aqueous solubility.

As used herein, melittin is masked if the modified peptide does not exhibit membrane activity and exhibits cell-specific (i.e. hepatocyte) targeting in vivo. Melittin is reversibly masked if cleavage of bonds linking the masking agents to the peptide results in restoration of amines on the peptide thereby restoring membrane activity.

It is another essential feature that the masking agents are covalently bound to melittin through physiologically labile reversible bonds. By using physiologically labile reversible linkages or bonds, the masking agents can be cleaved from the peptide in vivo, thereby unmasking the peptide and restoring activity of the unmasked peptide. By choosing an appropriate reversible linkage, it is possible to form a conjugate that restores activity of melittin after it has been delivered or targeted to a desired cell type or cellular location. Reversibility of the linkages provides for selective activation of melittin. Reversible covalent linkages contain reversible or labile bonds which may be selected from the group comprising: physiologically labile bonds, cellular physiologically labile bonds, pH labile bonds, very pH labile bonds, extremely pH labile bonds, and proetease cleavable bonds.

As used herein, a masking agent comprises a preferrably neutral (uncharged) compound having an ASGPr ligand and an amine-reactive group wherein reaction of the amine-reactive group with an amine on a peptide results in linkage of the ASGPr ligand to the peptide via a reversible physiologically labile covalent bond. Amine reactive groups are chosen such the cleavage in response to an appropriate physiological condition (e.g., reduced pH such as in an endosome/lysosome, or enzymatic cleavage such as in an endosome/lysosome) results in regeneration of the melittin amine. An ASGPr ligand is a group, typically a saccharide, having affinity for the asialoglycoprotein receptor. Preferred masking agents of the invention are able to modify the polymer (form a reversible bond with the polymer) in aqueous solution.

A preferred amine-reactive group comprises a disubstituted maleic anhydride. A preferred masking agent is represented by the structure:

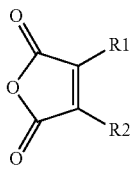

wherein in which R1 comprises an asialoglycoprotein receptor (ASGPr) ligand and R2 is an alkyl group such as a methyl ($—CH_3$) group, ethyl ($—CH_2CH_3$) group, or propyl ($—CH_2CH_2CH_3$) group.

In some embodiments, the galactose ligand is linked to the amine-reactive group through a PEG linker as illustrated by the structure:

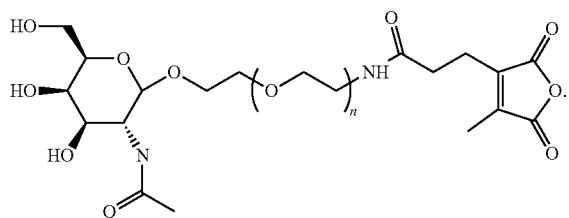

wherein n is an integer between 1 and 19.

Another preferred amine-reactive group comprises a dipeptide-amidobenzyl amine reactive carbonate derivative represented by the structure:

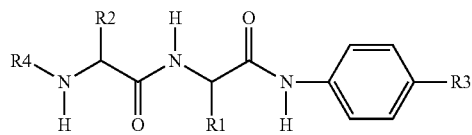

wherein:
R1 is the R group of amino acid 1,
R2 is the R group of amino acid 2,

R3 is $—CH_2—O—C(O)—O—Z$, wherein Z is halide,

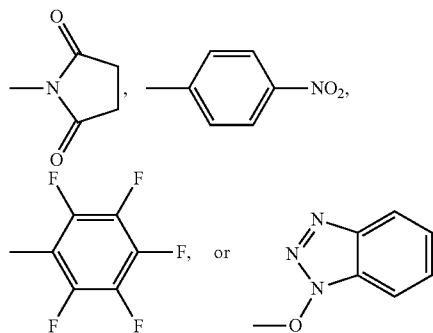
, 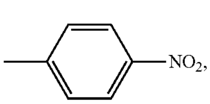 or 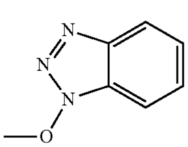 and R4 comprises the ASGPr ligand.

Reaction of the activated carbonate with a melittin amine connects the ASGPr ligand to the melittin peptide via a peptidase cleavable dipeptide-amidobenzyl carbamate linkage.

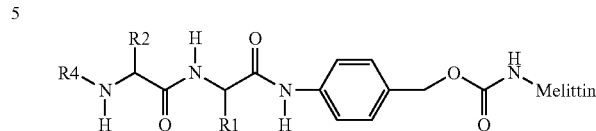

Enzymatic cleavage of the dipeptide removes the targeting ligand from the peptide and triggers an elimination reaction which results in regeneration of the peptide amine. While the structure above shows a single masking agent linked to a melittin peptide, in practice, several masking agents are linked to the melittin peptide; preferably such that more than 80% of the amines on a population of melittin peptides are modified.

Dipeptides Glu-Gly, Ala-Cit, Phe-Cit ("Cit" is the amino acid citrulline) are shown in Example 3. With respect to the above structure, Glu-Gly, Ala-Cit, Phe-Cit represent R2-R1. While charged amino acids are permissible, neutral amino acids are preferred. Other amino acid combinations are possible, provided they are cleaved by an endogenous protease. In addition, 3-5 amino acids may be used as the linker between the amido benzyl group and the targeting ligand.

As with maleic anhydride-based masking agents, the ASGPr ligand can be linked to the peptidase cleavable dipeptide-amidobenzyl carbonate via a PEG linker.

The membrane active polyamine can be conjugated to masking agents in the presence of an excess of masking agents. The excess masking agent may be removed from the conjugated delivery peptide prior to administration of the delivery peptide.

In another embodiment, the melittin peptides of the invention are further modified, at the amino or carboxyl termini, by covalent attachment of a steric stabilizer or an ASGPr ligand-steric stabilizer conjugate. Modification of the hydrophobic terminal end is preferred; the amino terminal end for melittin having "normal sequence" and the carboxyl terminal end for retro-melittin. A preferred steric stabilizer is a polyethylene glycol. The amino or carboxy terminal modifications may be linked to the peptide during synthesis using methods standard in the art. Alternatively, the amino or carboxy terminal modifications may be done through modification of cysteine residues on melittin peptides having amino or carboxy terminal cysteine residues. Preferred polyethylene glycols have 1-120 ethylene units. In another embodiment, preferred polyethylene glycols are less than 5 kDa in size. For ASGPr ligand-steric stabilizer conjugates (NAG-PEG modification), a preferred steric stabilizer is a polyethyleneglycol having 1-24 ethylene units. Terminal PEG modification, when combined with reversible masking, further reduces toxicity of the melittin delivery peptide. Terminal NAG-PEG modification enhances efficacy.

Steric Stabilizer

As used herein, a steric stabilizer is a non-ionic hydrophilic polymer (either natural, synthetic, or non-natural) that prevents or inhibits intramolecular or intermolecular interactions of a molecule to which it is attached relative to the molecule containing no steric stabilizer. A steric stabilizer hinders a molecule to which it is attached from engaging in electrostatic interactions. Electrostatic interaction is the non-covalent association of two or more substances due to attractive forces between positive and negative charges. Steric stabilizers can inhibit interaction with blood components and therefore opsonization, phagocytosis, and uptake by the reticuloendothelial system. Steric stabilizers can thus increase circulation time of molecules to which they are attached. Steric stabilizers can also inhibit aggregation of a molecule. A preferred steric stabilizer is a polyethylene glycol (PEG) or PEG derivative. PEG molecules suitable for the invention have about 1-120 ethylene glycol monomers.

ASGPr Ligand

Targeting moieties or groups enhance the pharmacokinetic or biodistribution properties of a conjugate to which they are attached to improve cell-specific distribution and cell-specific uptake of the conjugate. Galactose and galactose derivates have been used to target molecules to hepatocytes in vivo through their binding to the asialoglycoprotein receptor (ASGPr) expressed on the surface of hepatocytes. As used herein, a ASGPr ligand (or ASGPr ligand) comprises a galactose and galactose derivative having affinity for the ASGPr equal to or greater than that of galactose. Binding of galactose targeting moieties to the ASGPr(s) facilitates cell-specific targeting of the delivery peptide to hepatocytes and endocytosis of the delivery peptide into hepatocytes.

ASGPr ligands may be selected from the group comprising: lactose, galactose, N-acetylgalactosamine (GalNAc), galactosamine, N-formylgalactosamine, N-acetyl-galactosamine, N-propionylgalactosamine, N-n-butanoylgalactosamine, and N-iso-butanoyl-galactosamine (Iobst, S. T. and Drickamer, K. *J.B.C.* 1996, 271, 6686). ASGPr ligands can be monomeric (e.g., having a single galactosamine) or multimeric (e.g., having multiple galactosamines).

In one embodiment, the melittin peptide is reversibly masked by attachment of ASGPr ligand masking agents to ≥80% or ≥90% of primary amines on the peptide.

Labile Linkage

A linkage or linker is a connection between two atoms that links one chemical group or segment of interest to another chemical group or segment of interest via one or more covalent bonds. For example, a linkage can connect a masking agent to a peptide. Formation of a linkage may connect two separate molecules into a single molecule or it may connect two atoms in the same molecule. The linkage may be charge neutral or may bear a positive or negative charge. A reversible or labile linkage contains a reversible or labile bond. A linkage may optionally include a spacer that increases the distance between the two joined atoms. A spacer may further add flexibility and/or length to the linkage. Spacers may include, but are not be limited to, alkyl groups, alkenyl groups, alkynyl groups, aryl groups, aralkyl groups, aralkenyl groups, aralkynyl groups; each of which can contain one or more heteroatoms, heterocycles, amino acids, nucleotides, and saccharides. Spacer groups are well known in the art and the preceding list is not meant to limit the scope of the invention.

A labile bond is a covalent bond other than a covalent bond to a hydrogen atom that is capable of being selectively broken or cleaved under conditions that will not break or cleave other covalent bonds in the same molecule. More specifically, labile bond is a covalent bond that is less stable (thermodynamically) or more rapidly broken (kinetically) under appropriate conditions than other non-labile covalent bonds in the same molecule. Cleavage of a labile bond within a molecule may result in the formation of two molecules. For those skilled in the art, cleavage or lability of a bond is generally discussed in terms of half-life ($t_{1/2}$) of bond cleavage (the time required for half of the bonds to cleave). Thus, labile bonds encompass bonds that can be selectively cleaved more rapidly than other bonds a molecule.

Appropriate conditions are determined by the type of labile bond and are well known in organic chemistry. A labile bond can be sensitive to pH, oxidative or reductive conditions or agents, temperature, salt concentration, the presence of an enzyme (such as esterases, including nucleases, and proteases), or the presence of an added agent. For example, increased or decreased pH is the appropriate conditions for a pH-labile bond.

The rate at which a labile group will undergo transformation can be controlled by altering the chemical constituents of the molecule containing the labile group. For example, addition of particular chemical moieties (e.g., electron acceptors or donors) near the labile group can affect the particular conditions (e.g., pH) under which chemical transformation will occur.

As used herein, a physiologically labile bond is a labile bond that is cleavable under conditions normally encountered or analogous to those encountered within a mammalian body. Physiologically labile linkage groups are selected such that they undergo a chemical transformation (e.g., cleavage) when present in certain physiological conditions.

As used herein, a cellular physiologically labile bond is a labile bond that is cleavable under mammalian intracellular conditions. Mammalian intracellular conditions include chemical conditions such as pH, temperature, oxidative or reductive conditions or agents, and salt concentration found in or analogous to those encountered in mammalian cells. Mammalian intracellular conditions also include the presence of enzymatic activity normally present in a mammalian cell such as from proteolytic or hydrolytic enzymes. A cellular physiologically labile bond may also be cleaved in response to administration of a pharmaceutically acceptable exogenous agent. Physiologically labile bonds that are cleaved under appropriate conditions with a half life of less than 45 min. are considered very labile. Physiologically labile bonds that are cleaved under appropriate conditions with a half life of less than 15 min are considered extremely labile.

Chemical transformation (cleavage of the labile bond) may be initiated by the addition of a pharmaceutically acceptable agent to the cell or may occur spontaneously when a molecule containing the labile bond reaches an appropriate intra- and/or extra-cellular environment. For example, a pH labile bond may be cleaved when the molecule enters an acidified endosome. Thus, a pH labile bond may be considered to be an endosomal cleavable bond. Enzyme cleavable bonds may be cleaved when exposed to enzymes such as those present in an endosome or lysosome or in the cytoplasm. A disulfide bond may be cleaved when the molecule enters the more reducing environment of the cell cytoplasm. Thus, a disulfide may be considered to be a cytoplasmic cleavable bond.

As used herein, a pH-labile bond is a labile bond that is selectively broken under acidic conditions (pH<7). Such bonds may also be termed endosomally labile bonds, since cell endosomes and lysosomes have a pH less than 7. The term pH-labile includes bonds that are pH-labile, very pH-labile, and extremely pH-labile.

Reaction of an anhydride with an amine forms an amide and an acid. For many anhydrides, the reverse reaction (formation of an anhydride and amine) is very slow and energetically unfavorable. However, if the anhydride is a cyclic anhydride, reaction with an amine yields an amide acid, a molecule in which the amide and the acid are in the same molecule. The presence of both reactive groups (the amide and the carboxylic acid) in the same molecule accelerates the reverse reaction. In particular, the product of primary amines with maleic anhydride and maleic anhydride derivatives, maleamic acids, revert back to amine and anhydride $1 \times 10^9$ to $1 \times 10^{13}$ times faster than its noncyclic analogues (Kirby 1980).

Reaction of an amine with an anhydride to form an amide and an acid.

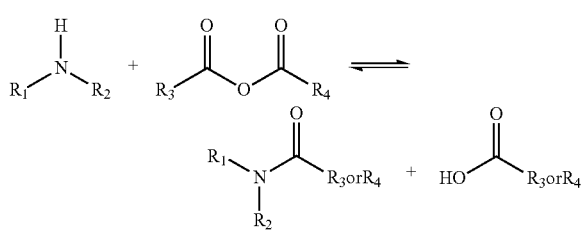

Reaction of an amine with a cyclic anhydride to form an amide acid.

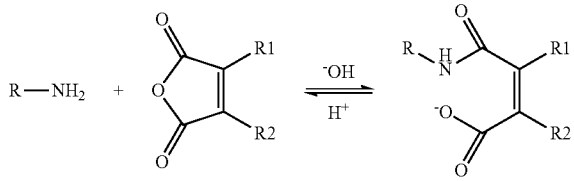

Cleavage of the amide acid to form an amine and an anhydride is pH-dependent and is greatly accelerated at acidic pH. This pH-dependent reactivity can be exploited to form reversible pH-labile bonds and linkers. Cis-aconitic acid has been used as such a pH-sensitive linker molecule. The γ-carboxylate is first coupled to a molecule. In a second step, either the α or β carboxylate is coupled to a second molecule to form a pH-sensitive coupling of the two molecules. The half life for cleavage of this linker at pH 5 is between 8 and 24 h.

Structures of cis-aconitic anhydride and maleic anhydride.

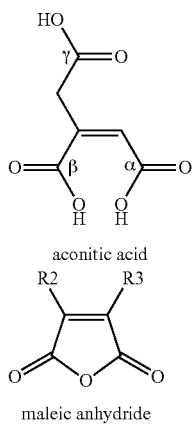

The pH at which cleavage occurs is controlled by the addition of chemical constituents to the labile moiety. The rate of conversion of maleamic acids to amines and maleic anhydrides is strongly dependent on substitution (R2 and R3) of the maleic anhydride system. When R2 is methyl, the rate of conversion is 50-fold higher than when R2 and R3 are hydrogen. When there are alkyl substitutions at both R2 and R3 (e.g., 2,3-dimethylmaleicanhydride) the rate increase is dramatic: 10,000-fold faster than non-substituted maleic anhydride. The maleamate bond formed from the modification of an amine with 2,3-dimethylmaleic anhydride is cleaved to restore the anhydride and amine with a half-life between 4 and 10 min at pH 5. It is anticipated that if R2 and R3 are groups larger than hydrogen, the rate of amide-acid conversion to amine and anhydride will be faster than if R2 and/or R3 are hydrogen.

Very pH-labile bond: A very pH-labile bond has a half-life for cleavage at pH 5 of less than 45 min. The construction of very pH-labile bonds is well-known in the chemical art.

Extremely pH-labile bonds: An extremely pH-labile bond has a half-life for cleavage at pH 5 of less than 15 min. The construction of extremely pH-labile bonds is well-known in the chemical art.

Disubstituted cyclic anhydrides are particularly useful for attachment of masking agents to melittin peptides of the invention. They provide physiologically pH-labile linkages, readily modify amines, and restore those amines upon cleavage in the reduced pH found in cellular endosomes and lysosome. Second, the α or β carboxylic acid group created upon reaction with an amine, appears to contribute only about $1/20^{th}$ of the expected negative charge to the polymer (Rozema et al. Bioconjugate Chemistry 2003). Thus, modification of the peptide with the disubstituted maleic anhydrides effectively neutralizes the positive charge of the peptide rather than creates a peptide with high negative charge. Near neutral delivery peptides are preferred for in vivo delivery.

RNAi Polynucleotide Conjugate

We have found that conjugation of an RNAi polynucleotide to a polynucleotide targeting moiety, either a hydrophobic group or to a galactose cluster, and co-administration of the RNAi polynucleotide conjugate with the delivery peptide described above provides for efficient, functional delivery of the RNAi polynucleotide to liver cells, particularly hepatocytes, in vivo. By functional delivery, it is meant that the RNAi polynucleotide is delivered to the cell and has the expected biological activity, sequence-specific inhibition of gene expression. Many molecules, including polynucleotides, administered to the vasculature of a mammal are normally cleared from the body by the liver. Clearance of a polynucleotide by the liver wherein the polynucleotide is degraded or otherwise processed for removal from the body and wherein the polynucleotide does not cause sequence-specific inhibition of gene expression is not considered functional delivery.

The RNAi polynucleotide conjugate is formed by covalently linking the RNAi polynucleotide to the polynucleotide targeting moiety. The polynucleotide is synthesized or modified such that it contains a reactive group A. The targeting moiety is also synthesized or modified such that it contains a reactive group B. Reactive groups A and B are chosen such that they can be linked via a covalent linkage using methods known in the art.

The targeting moiety may be linked to the 3' or the 5' end of the RNAi polynucleotide. For siRNA polynucleotides, the targeting moiety may be linked to either the sense strand or the antisense strand, though the sense strand is preferred.

In one embodiment, the polynucleotide targeting moiety consists of a hydrophobic group More specifically, the polynucleotide targeting moiety consists of a hydrophobic group having at least 20 carbon atoms. Hydrophobic groups used as polynucleotide targeting moieties are herein referred to as hydrophobic targeting moieties. Exemplary suitable hydrophobic groups may be selected from the group comprising: cholesterol, dicholesterol, tocopherol, ditocopherol, didecyl, didodecyl, dioctadecyl, didodecyl, dioctadecyl, isoprenoid, and choleamide. Hydrophobic groups having 6 or fewer carbon atoms are not effective as polynucleotide targeting moieties, while hydrophobic groups having 8 to 18 carbon atoms provide increasing polynucleotide delivery with increasing size of the hydrophobic group (i.e. increasing number of carbon atoms). Attachment of a hydrophobic targeting moiety to an RNAi polynucleotide does not provide efficient functional in vivo delivery of the RNAi polynucleotide in the absence of co-administration of the delivery peptide. While siRNA-cholesterol conjugates have been reported by others to deliver siRNA (siRNA-cholesterol) to liver cells in vivo, in the absence of any additional delivery vehicle, high concentrations of siRNA are required and delivery efficacy is poor. When combined with the delivery peptides described herein, delivery of the polynucleotide is greatly improved. By providing the siRNA-cholesterol together with a delivery peptide of the invention, efficacy of siRNA-cholesterol is increased about 100 fold.

Hydrophobic groups useful as polynucleotide targeting moieties may be selected from the group consisting of: alkyl group, alkenyl group, alkynyl group, aryl group, aralkyl group, aralkenyl group, and aralkynyl group, each of which may be linear, branched, or cyclic, cholesterol, cholesterol derivative, sterol, steroid, and steroid derivative. Hydrophobic targeting moieties are preferably hydrocarbons, containing only carbon and hydrogen atoms. However, substitutions or heteroatoms which maintain hydrophobicity, for example fluorine, may be permitted. The hydrophobic targeting moiety may be attached to the 3' or 5' end of the RNAi polynucleotide using methods known in the art. For RNAi polynucleotides having 2 strands, such as siRNA, the hydrophobic group may be attached to either strand.

In another embodiment, the polynucleotide targeting moiety comprises a galactose cluster (galactose cluster targeting moiety). As used herein, a galactose cluster comprises a molecule having two to four terminal galactose derivatives. As used herein, the term galactose derivative includes both galactose and derivatives of galactose having affinity for the asialoglycoprotein receptor equal to or greater than that of galactose. A terminal galactose derivative is attached to a molecule through its C-1 carbon. The asialoglycoprotein receptor (ASGPr) is unique to hepatocytes and binds branched galactose-terminal glycoproteins. A preferred galactose cluster has three terminal galactosamines or galactosamine derivatives each having affinity for the asialoglycoprotein receptor. A more preferred galactose cluster has three terminal N-acetyl-galactosamines. Other terms common in the art include tri-antennary galactose, tri-valent galactose and galactose trimer. It is known that tri-antennary galactose derivative clusters are bound to the ASGPr with greater affinity than bi-antennary or mono-antennary galactose derivative structures (Baenziger and Fiete, 1980, Cell, 22, 611-620; Connolly et al., 1982, J. Biol. Chem., 257, 939-945). Mulivalency is required to achieve nM affinity. The attachment of a single galactose derivative having affinity for the asialoglycoprotein receptor does not enable functional delivery of the RNAi polynucleotide to hepatocytes in vivo when co-administered with the delivery peptide.

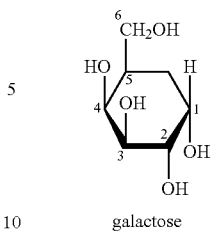

galactose

A galactose cluster contains three galactose derivatives each linked to a central branch point. The galactose derivatives are attached to the central branch point through the C-1 carbons of the saccharides. The galactose derivative is preferably linked to the branch point via linkers or spacers. A preferred spacer is a flexible hydrophilic spacer (U.S. Pat. No. 5,885,968; Biessen et al. J. Med. Chem. 1995 Vol. 39 p. 1538-1546). A preferred flexible hydrophilic spacer is a PEG spacer. A preferred PEG spacer is a $PEG_3$ spacer. The branch point can be any small molecule which permits attachment of the three galactose derivatives and further permits attachment of the branch point to the RNAi polynucleotide. An exemplary branch point group is a di-lysine. A di-lysine molecule contains three amine groups through which three galactose derivatives may be attached and a carboxyl reactive group through which the di-lysine may be attached to the RNAi polynucleotide. Attachment of the branch point to the RNAi polynucleotide may occur through a linker or spacer. A preferred spacer is a flexible hydrophilic spacer. A preferred flexible hydrophilic spacer is a PEG spacer. A preferred PEG spacer is a $PEG_3$ spacer (three ethylene units). The galactose cluster may be attached to the 3' or 5' end of the RNAi polynucleotide using methods known in the art. For RNAi polynucleotides having 2 strands, such as siRNA, the galactose cluster may be attached to either strand.

A preferred galactose derivative is an N-acetyl-galactosamine (GalNAc). Other saccharides having affinity for the asialoglycoprotein receptor may be selected from the list comprising: galactose, galactosamine, N-formylgalactosamine, N-acetylgalactosamine, N-propionyl-galactosamine, N-n-butanoylgalactosamine, and N-iso-butanoylgalactos-amine. The affinities of numerous galactose derivatives for the asialoglycoprotein receptor have been studied (see for example: Iobst, S. T. and Drickamer, K. *J.B.C.* 1996, 271, 6686) or are readily determined using methods typical in the art.

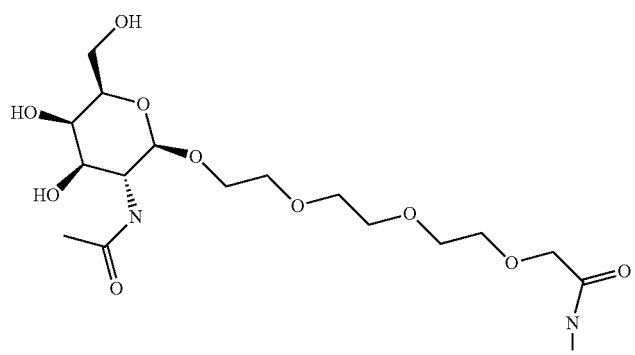

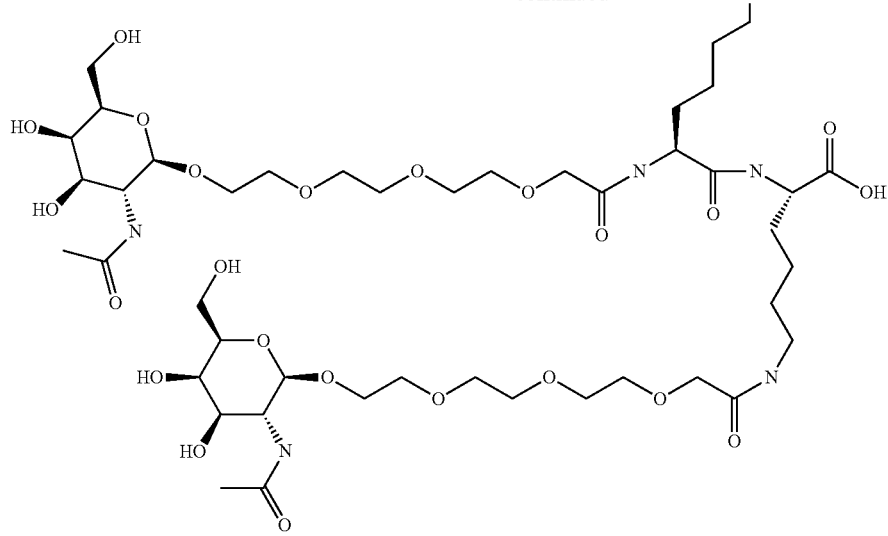

One embodiment of a Galactose cluster

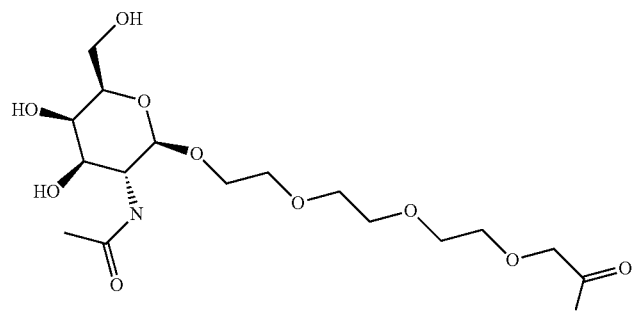

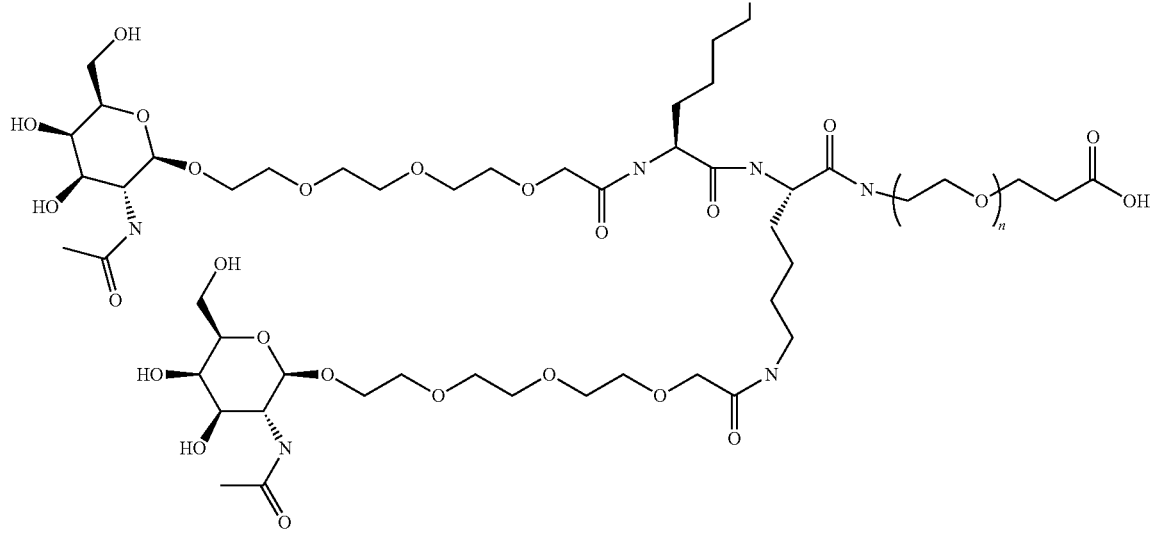

Galactose cluster with PEG spacer between branch point and nucleic acid

The term polynucleotide, or nucleic acid or polynucleic acid, is a term of art that refers to a polymer containing at least two nucleotides. Nucleotides are the monomeric units of polynucleotide polymers. Polynucleotides with less than 120 monomeric units are often called oligonucleotides. Natural nucleic acids have a deoxyribose- or ribose-phosphate backbone. A non-natural or synthetic polynucleotide is a polynucleotide that is polymerized in vitro or in a cell free system and contains the same or similar bases but may contain a backbone of a type other than the natural ribose or deoxyribose-phosphate backbone. Polynucleotides can be synthesized using any known technique in the art. Polynucleotide backbones known in the art include: PNAs (peptide nucleic acids), phosphorothioates, phosphorodiamidates, morpholinos, and other variants of the phosphate backbone of native nucleic acids. Bases include purines and pyrimidines, which further include the natural compounds adenine, thymine, guanine, cytosine, uracil, inosine, and natural analogs. Synthetic derivatives of purines and pyrimidines include, but are not limited to, modifications which place new reactive groups on the nucleotide such as, but not limited to, amines, alcohols, thiols, carboxylates, and alkylhalides. The term base encompasses any of the known base analogs of DNA and RNA. A polynucleotide may contain ribonucleotides, deoxyribonucleotides, synthetic nucleotides, or any suitable combination. Polynucleotides may be polymerized in vitro, they may be recombinant, contain chimeric sequences, or derivatives of these groups. A polynucleotide may include a terminal cap moiety at the 5'-end, the 3'-end, or both the 5' and 3' ends. The cap moiety can be, but is not limited to, an inverted deoxy abasic moiety, an inverted deoxy thymidine moiety, a thymidine moiety, or 3' glyceryl modification.

An RNA interference (RNAi) polynucleotide is a molecule capable of inducing RNA interference through interaction with the RNA interference pathway machinery of mammalian cells to degrade or inhibit translation of messenger RNA (mRNA) transcripts of a transgene in a sequence specific manner. Two primary RNAi polynucleotides are small (or short) interfering RNAs (siRNAs) and micro RNAs (miRNAs). RNAi polynucleotides may be selected from the group comprising: siRNA, microRNA, double-strand RNA (dsRNA), short hairpin RNA (shRNA), and expression cassettes encoding RNA capable of inducing RNA interference. siRNA comprises a double stranded structure typically containing 15-50 base pairs and preferably 21-25 base pairs and having a nucleotide sequence identical (perfectly complementary) or nearly identical (partially complementary) to a coding sequence in an expressed target gene or RNA within the cell. An siRNA may have dinucleotide 3' overhangs. An siRNA may be composed of two annealed polynucleotides or a single polynucleotide that forms a hairpin structure. An siRNA molecule of the invention comprises a sense region and an antisense region. In one embodiment, the siRNA of the conjugate is assembled from two oligonucleotide fragments wherein one fragment comprises the nucleotide sequence of the antisense strand of the siRNA molecule and a second fragment comprises nucleotide sequence of the sense region of the siRNA molecule. In another embodiment, the sense strand is connected to the antisense strand via a linker molecule, such as a polynucleotide linker or a non-nucleotide linker. MicroRNAs (miRNAs) are small noncoding RNA gene products about 22 nucleotides long that direct destruction or translational repression of their mRNA targets.

If the complementarity between the miRNA and the target mRNA is partial, translation of the target mRNA is repressed. If complementarity is extensive, the target mRNA is cleaved. For miRNAs, the complex binds to target sites usually located in the 3' UTR of mRNAs that typically share only partial homology with the miRNA. A "seed region"—a stretch of about seven (7) consecutive nucleotides on the 5' end of the miRNA that forms perfect base pairing with its target—plays a key role in miRNA specificity. Binding of the RISC/miRNA complex to the mRNA can lead to either the repression of protein translation or cleavage and degradation of the mRNA. Recent data indicate that mRNA cleavage happens preferentially if there is perfect homology along the whole length of the miRNA and its target instead of showing perfect base-pairing only in the seed region (Pillai et al. 2007).

RNAi polynucleotide expression cassettes can be transcribed in the cell to produce small hairpin RNAs that can function as siRNA, separate sense and anti-sense strand linear siRNAs, or miRNA. RNA polymerase III transcribed DNAs contain promoters selected from the list comprising: U6 promoters, H1 promoters, and tRNA promoters. RNA polymerase II promoters include U1, U2, U4, and U5 promoters, snRNA promoters, microRNA promoters, and mRNA promoters.

Lists of known miRNA sequences can be found in databases maintained by research organizations such as Wellcome Trust Sanger Institute, Penn Center for Bioinformatics, Memorial Sloan Kettering Cancer Center, and European Molecule Biology Laboratory, among others. Known effective siRNA sequences and cognate binding sites are also well represented in the relevant literature. RNAi molecules are readily designed and produced by technologies known in the art. In addition, there are computational tools that increase the chance of finding effective and specific sequence motifs (Pei et al. 2006, Reynolds et al. 2004, Khvorova et al. 2003, Schwarz et al. 2003, Ui-Tei et al. 2004, Heale et al. 2005, Chalk et al. 2004, Amarzguioui et al. 2004).

The polynucleotides of the invention can be chemically modified. Non-limiting examples of such chemical modifications include: phosphorothioate internucleotide linkages, 2'-O-methyl ribonucleotides, 2'-deoxy-2'-fluoro ribonucleotides, 2'-deoxy ribonucleotides, "universal base" nucleotides, 5-C-methyl nucleotides, and inverted deoxyabasic residue incorporation. These chemical modifications, when used in various polynucleotide constructs, are shown to preserve polynucleotide activity in cells while at the same time increasing the serum stability of these compounds. Chemically modified siRNA can also minimize the possibility of activating interferon activity in humans.

In one embodiment, a chemically-modified RNAi polynucleotide of the invention comprises a duplex having two strands, one or both of which can be chemically-modified, wherein each strand is about 19 to about 29 nucleotides. In one embodiment, an RNAi polynucleotide of the invention comprises one or more modified nucleotides while maintaining the ability to mediate RNAi inside a cell or reconstituted in vitro system. An RNAi polynucleotide can be modified wherein the chemical modification comprises one or more (e.g., about 1, 2, 3, 4, 5, 6, 7, 8, 9, 10, or more) of the nucleotides. An RNAi polynucleotide of the invention can comprise modified nucleotides as a percentage of the total number of nucleotides present in the RNAi polynucleotide. As such, an RNAi polynucleotide of the invention can generally comprise modified nucleotides from about 5 to about 100% of the nucleotide positions (e.g., 5%, 10%, 15%, 20%, 25%, 30%, 35%, 40%, 45%, 50%, 55%, 60%, 65%, 70%, 75%, 80%, 85%, 90%, 95% or 100% of the nucleotide positions). The actual percentage of modified nucleotides present in a given RNAi polynucleotide depends on the total number of nucleotides present in the RNAi polynucleotide. If the RNAi polynucleotide is single stranded, the percent modification can be based upon the total number of nucleotides present in the single stranded RNAi polynucleotide. Likewise, if the RNAi polynucleotide is double stranded, the percent modification can be based upon the total number of nucleotides present in the sense strand, antisense strand, or both the sense and antisense strands. In addition, the actual percentage of modified nucleotides present in a given RNAi polynucleotide can also depend on the total number of purine and pyrimidine nucleotides present in the RNAi polynucleotide. For example, wherein all pyrimidine nucleotides and/or all purine nucleotides present in the RNAi polynucleotide are modified.

An RNAi polynucleotide modulates expression of RNA encoded by a gene. Because multiple genes can share some degree of sequence homology with each other, an RNAi polynucleotide can be designed to target a class of genes with sufficient sequence homology. Thus, an RNAi polynucleotide can contain a sequence that has complementarity to sequences that are shared amongst different gene targets or are unique for a specific gene target. Therefore, the RNAi polynucleotide can be designed to target conserved regions of an RNA sequence having homology between several genes thereby targeting several genes in a gene family (e.g., different gene isoforms, splice variants, mutant genes, etc.). In another embodiment, the RNAi polynucleotide can be designed to target a sequence that is unique to a specific RNA sequence of a single gene.

The term complementarity refers to the ability of a polynucleotide to form hydrogen bond(s) with another polynucleotide sequence by either traditional Watson-Crick or other non-traditional types. In reference to the polynucleotide molecules of the present invention, the binding free energy for a polynucleotide molecule with its target (effector binding site) or complementary sequence is sufficient to allow the relevant function of the polynucleotide to proceed, e.g., enzymatic mRNA cleavage or translation inhibition. Determination of binding free energies for nucleic acid molecules is well known in the art (Frier et al. 1986, Turner et al. 1987). A percent complementarity indicates the percentage of bases, in a contiguous strand, in a first polynucleotide molecule which can form hydrogen bonds (e.g., Watson-Crick base pairing) with a second polynucleotide sequence (e.g., 5, 6, 7, 8, 9, 10 out of 10 being 50%, 60%, 70%, 80%, 90%, and 100% complementary). Perfectly complementary means that all the bases in a contiguous strand of a polynucleotide sequence will hydrogen bond with the same number of contiguous bases in a second polynucleotide sequence.

By inhibit, down-regulate, or knockdown gene expression, it is meant that the expression of the gene, as measured by the level of RNA transcribed from the gene or the level of polypeptide, protein or protein subunit translated from the RNA, is reduced below that observed in the absence of the blocking polynucleotide-conjugates of the invention. Inhibition, down-regulation, or knockdown of gene expression, with a polynucleotide delivered by the compositions of the invention, is preferably below that level observed in the presence of a control inactive nucleic acid, a nucleic acid with scrambled sequence or with inactivating mismatches, or in absence of conjugation of the polynucleotide to the masked polymer.

In Vivo Administration

In pharmacology and toxicology, a route of administration is the path by which a drug, fluid, poison, or other substance is brought into contact with the body. In general, methods of administering drugs and nucleic acids for treatment of a mammal are well known in the art and can be applied to administration of the compositions of the invention. The compounds of the present invention can be administered via any suitable route, most preferably parenterally, in a preparation appropriately tailored to that route. Thus, the compounds of the present invention can be administered by injection, for example, intravenously, intramuscularly, intracutaneously, subcutaneously, or intraperitoneally. Accordingly, the present invention also provides pharmaceutical compositions comprising a pharmaceutically acceptable carrier or excipient.

Parenteral routes of administration include intravascular (intravenous, intraarterial), intramuscular, intraparenchymal, intradermal, subdermal, subcutaneous, intratumor, intraperitoneal, intrathecal, subdural, epidural, and intralymphatic injections that use a syringe and a needle or catheter. Intravascular herein means within a tubular structure called a vessel that is connected to a tissue or organ within the body. Within the cavity of the tubular structure, a bodily fluid flows to or from the body part. Examples of bodily fluid include blood, cerebrospinal fluid (CSF), lymphatic fluid, or bile. Examples of vessels include arteries, arterioles, capillaries, venules, sinusoids, veins, lymphatics, bile ducts, and ducts of the salivary or other exocrine glands. The intravascular route includes delivery through the blood vessels such as an artery or a vein. The blood circulatory system provides systemic spread of the pharmaceutical.

The described compositions are injected in pharmaceutically acceptable carrier solutions. Pharmaceutically acceptable refers to those properties and/or substances which are acceptable to the mammal from a pharmacological/toxicological point of view. The phrase pharmaceutically acceptable refers to molecular entities, compositions, and properties that are physiologically tolerable and do not typically produce an allergic or other untoward or toxic reaction when administered to a mammal. Preferably, as used herein, the term pharmaceutically acceptable means approved by a regulatory agency of the Federal or a state government or listed in the U.S. Pharmacopeia or other generally recognized pharmacopeia for use in animals and more particularly in humans.

The RNAi polynucleotide-targeting moiety conjugate is co-administered with the delivery peptide. By co-administered it is meant that the RNAi polynucleotide and the delivery peptide are administered to the mammal such that both are present in the mammal at the same time. The RNAi polynucleotide-targeting moiety conjugate and the delivery peptide may be administered simultaneously or they may be delivered sequentially. For simultaneous administration, they may be mixed prior to administration. For sequential administration, either the RNAi polynucleotide-targeting moiety conjugate or the delivery peptide may be administered first.

For RNAi polynucleotide-hydrophobic targeting moiety conjugates, the RNAi conjugate may be administered up to 30 minutes prior to administration of the delivery peptide. Also for RNAi polynucleotide-hydrophobic targeting moiety conjugates, the delivery peptide may be administered up to two hours prior to administration of the RNAi conjugate.

For RNAi polynucleotide-galactose cluster targeting moiety conjugates, the RNAi conjugate may be administered up to 15 minutes prior to administration of the delivery peptide. Also for RNAi polynucleotide-galactose cluster targeting moiety conjugates, the delivery peptide may be administered up to 15 minutes prior to administration of the RNAi conjugate.

Therapeutic Effect

RNAi polynucleotides may be delivered for research purposes or to produce a change in a cell that is therapeutic. In vivo delivery of RNAi polynucleotides is useful for research reagents and for a variety of therapeutic, diagnostic, target validation, genomic discovery, genetic engineering, and pharmacogenomic applications. We have disclosed RNAi polynucleotide delivery resulting in inhibition of endogenous gene expression in hepatocytes. Levels of a reporter (marker) gene expression measured following delivery of a polynucleotide indicate a reasonable expectation of similar levels of gene expression following delivery of other polynucleotides. Levels of treatment considered beneficial by a person having ordinary skill in the art differ from disease to disease. For example, Hemophilia A and B are caused by deficiencies of the X-linked clotting factors VIII and IX, respectively. Their clinical course is greatly influenced by the percentage of normal serum levels of factor VIII or IX: <2%, severe; 2-5%, moderate; and 5-30% mild. Thus, an increase from 1% to 2% of the normal level of circulating factor in severe patients can be considered beneficial. Levels greater than 6% prevent spontaneous bleeds but not those secondary to surgery or injury. Similarly, inhibition of a gene need not be 100% to provide a therapeutic benefit. A person having ordinary skill in the art of gene therapy would reasonably anticipate beneficial levels of expression of a gene specific for a disease based upon sufficient levels of marker gene results. In the hemophilia example, if marker genes were expressed to yield a protein at a level comparable in volume to 2% of the normal level of factor VIII, it can be reasonably expected that the gene coding for factor VIII would also be expressed at similar levels. Thus, reporter or marker genes serve as useful paradigms for expression of intracellular proteins in general.

The liver is one of the most important target tissues for gene therapy given its central role in metabolism (e.g., lipoprotein metabolism in various hypercholesterolemias) and the secretion of circulating proteins (e.g., clotting factors in hemophilia). In addition, acquired disorders such as chronic hepatitis (e.g. hepatitis B virus infection) and cirrhosis are common and are also potentially treated by polynucleotide-based liver therapies. A number of diseases or conditions which affect or are affected by the liver are potentially treated through knockdown (inhibition) of gene expression in the liver. Such liver diseases and conditions may be selected from the list comprising: liver cancers (including hepatocellular carcinoma, HCC), viral infections (including hepatitis), metabolic disorders, (including hyperlipidemia and diabetes), fibrosis, and acute liver injury.

The amount (dose) of delivery peptide and RNAi-polynucleotide-conjugate that is to be administered can be determined empirically. We have shown effective knockdown of gene expression using 0.1-10 mg/kg animal weight of siRNA-conjugate and 5-60 mg/kg animal weight delivery peptide. A preferred amount in mice is 0.25-2.5 mg/kg siRNA-conjugate and 10-40 mg/kg delivery peptide. More preferably, about 12.5-20 mg/kg delivery peptide is administered. The amount of RNAi polynucleotide-conjugate is easily increased because it is typically not toxic in larger doses.

As used herein, in vivo means that which takes place inside an organism and more specifically to a process performed in or on the living tissue of a whole, living multicellular organism (animal), such as a mammal, as opposed to a partial or dead one.

EXAMPLES

Example 1

Melittin Synthesis

All melittin peptides were made using peptide synthesis techniques standard in the art. Suitable melittin peptides can be all L-form amino acids, all D-form amino acids (inverso). Independently of L or D form, the melittin peptide sequence can be reversed (retro).

Example 2

Melittin Modification

Amino terminal Modification of Melittin Derivatives. Solutions of CKLK-Melittin (20 mg/ml), TCEP-HCl (28.7 mg/ml, 100 mM), and MES-Na (21.7 mg/ml, 100 mM) were prepared in $dH_2O$. In a 20 ml scintillation vial, CKLK-Melittin (0.030 mmol, 5 ml) was reacted with 1.7 molar equivalents TCEP-HCl (0.05 μmol, 0.51 ml) and left to stir at room temperature for 30 min. MES-Na (2 ml) and Water (1.88 ml) were then added in amounts to yield final concentrations of 10 mg/ml Melittin and 20 mM MES-Na. The pH was checked and adjusted to pH 6.5-7. A solution of NAG-$PEG_2$-Br (100 mg/ml) was prepared in $dH_2O$, NAG-$PEG_2$-Br (4.75 eq, 0.142 mmol, 0.61 ml) was added, and the solution was left to stir at room temperature for 48 h.

Alternatively, in a 20 ml scintillation vial, Cys-Melittin (0.006 mmol, 1 ml) was reacted with 1.7 molar equivalents TCEP-HCl (0.010 mmol, 100 μl) and left to stir at room temperature for 30 min. MES-Na (400 μl) and water (390 μl) were added in amounts to yield final concentrations of 10 mg/ml Melittin and 20 mM MES-Na. The pH was checked and adjusted to pH 6.5-7. A solution of NAG-$PEG_8$-Maleimide (100 mg/ml) was prepared in $dH_2O$, NAG-$PEG_8$-Maleimide (2 eq, 0.012 mmol, 110 μl) was added, and the solution was left to stir at room temperature for 48 h.

Samples were purified on a Luna 10μ, C18 100 Å 21.2×250 mm column. Buffer A: $H_2O$ 0.1% TFA and Buffer B: MeCN, 10% Isopropyl Alcohol, 0.1% TFA. Flow rate of 15 ml/min, 35% A to 62.5% B in 20 min.

Other amino terminal modifications were made using similar means. Carboxyl terminal modifications were made substituting melittin peptides having carboxyl terminal cysteines for melittins having amino terminal cysteines.

Compounds used to modified Cys-Melittin or Melittin-Cys:

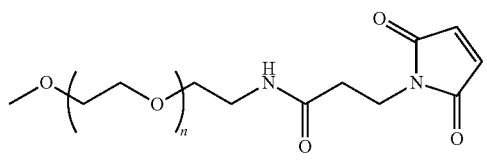

PEG maleimide n is an integer from 1 to 120 (PEG molecular weight up to about 5 kDa)

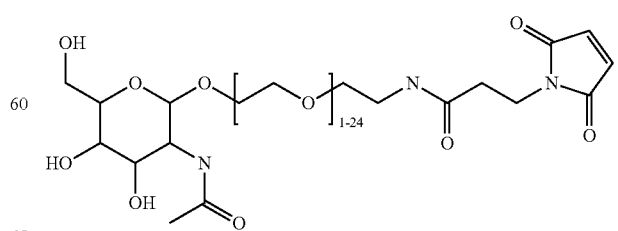

NAG-PEG maleimide

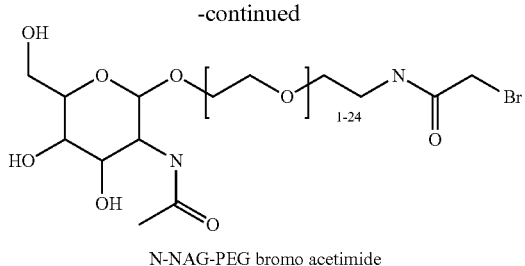

N-NAG-PEG bromo acetimide

Peptides having acetyl, dimethyl, stearoyl, myristoyl, and PEG amino or carboxyl terminal modifications, but not terminal cysteine residues, were generated on resin during peptide synthesis using methods typical in the art.

Example 3

Masking Agents Synthesis

A. pH labile masking agents: Steric stabilizer CDM-PEG and targeting group CDM-NAG (N-acetyl galactosamine) Syntheses. To a solution of CDM (300 mg, 0.16 mmol) in 50 mL methylene chloride was added oxalyl chloride (2 g, 10 wt. eq.) and dimethylformamide (5 µl). The reaction was allowed to proceed overnight, after which the excess oxalyl chloride and methylene chloride were removed by rotary evaporation to yield the CDM acid chloride. The acid chloride was dissolved in 1 mL of methylene chloride. To this solution was added 1.1 molar equivalents polyethylene glycol monomethyl ether (MW average 550) for CDM-PEG or (aminoethoxy)ethoxy-2-(acetylamino)-2-deoxy-β-D-galactopyranoside (i.e. amino bisethoxyl-ethyl NAG) for CDM-NAG, and pyridine (200 µl, 1.5 eq) in 10 mL of methylene chloride. The solution was then stirred 1.5 h. The solvent was then removed and the resulting solid was dissolved into 5 mL of water and purified using reverse-phase HPLC using a 0.1% TFA water/acetonitrile gradient.

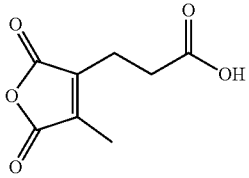

CDM

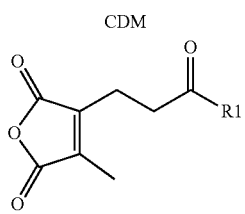

Generic Disubstituted Maleic Anhydride Masking Agent

R1 comprises a neutral ASGPr ligand. Preferably the Masking Agent in uncharged.

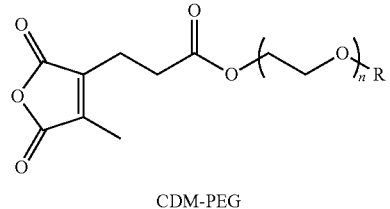

CDM-PEG

R is a methyl or ethyl, and n is an integer from 2 to 100. Preferably, the PEG contains from 5 to 20 ethylene units (n is an integer from 5 to 20). More preferably, PEG contains 10-14 ethylene units (n is an integer from 10 to 14). The PEG may be of variable length and have a mean length of 5-20 or 10-14 ethylene units. Alternatively, the PEG may be monodisperse, uniform or discrete; having, for example, exactly 11 or 13 ethylene units.

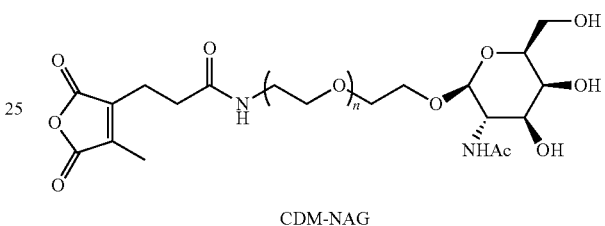

CDM-NAG n is an integer from 1 to 10. As shown above, a PEG spacer may be positioned between the anhydride group and the ASGPr ligand. A preferred PEG spacer contains 1-10 ethylene units.

Alternatively an alkyl spacer may be used between the anhydride and the N-Acetylgalactosamine.

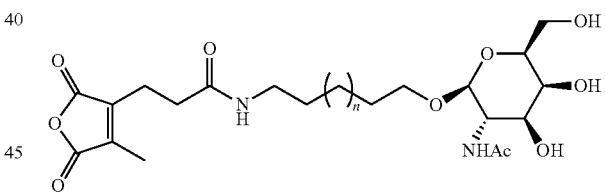

CDM-NAG (alkyl spacer)

n is a integer from 0 to 6.

Other spacers or linkers may be used bet between the anhydride and the N-Acetyl-galactosamine. However, a hydrophilic, neutral (preferably uncharged) spacer or linker is preferred)

B. Protease (Peptidase) Cleavable Masking Agents. Melittin peptide can also be reversibly modified using specialized enzyme cleavable linkers. These enzyme cleavable linkers employ a dipeptide connected to an amidobenzyl activated carbonate moiety. Reaction of the activated carbonate with a peptide amine connects a targeting compound, such as asialoglycoprotein receptor ligand, to the melittin peptide via a peptidase cleavable dipeptide-amidobenzyl carbamate linkage. Enzyme cleavage of the dipeptide removes the targeting ligand from the peptide and triggers an elimination reaction which results in regeneration of the peptide amine. The following enzymatically cleavable linkers were synthesized:

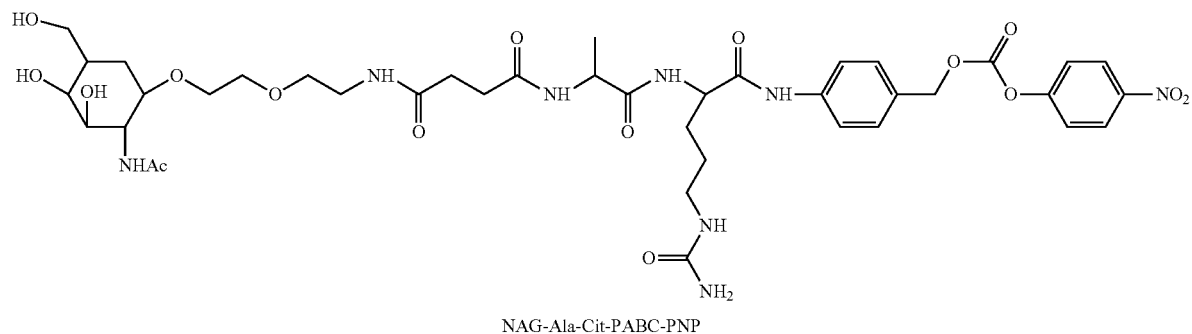
NAG-Ala-Cit-PABC-PNP
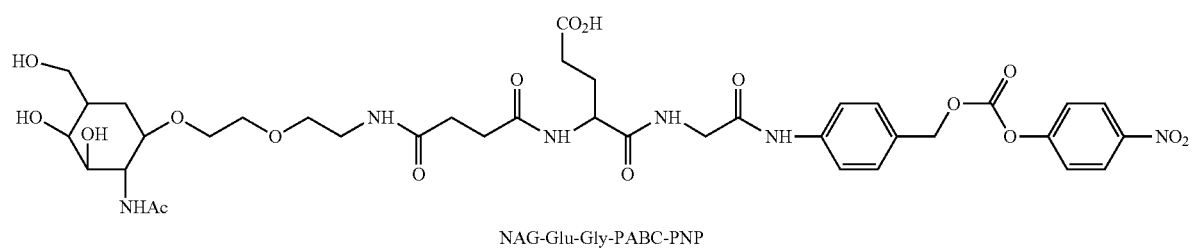
NAG-Glu-Gly-PABC-PNP
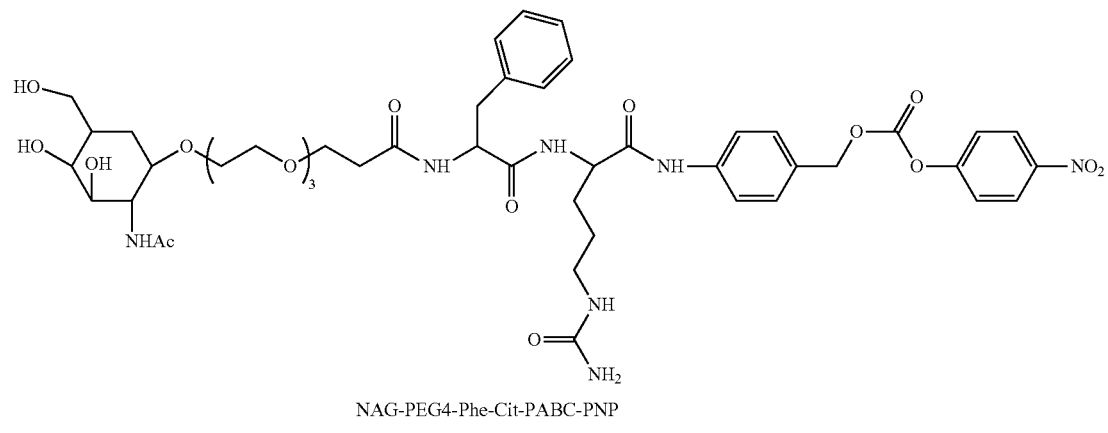
NAG-PEG4-Phe-Cit-PABC-PNP
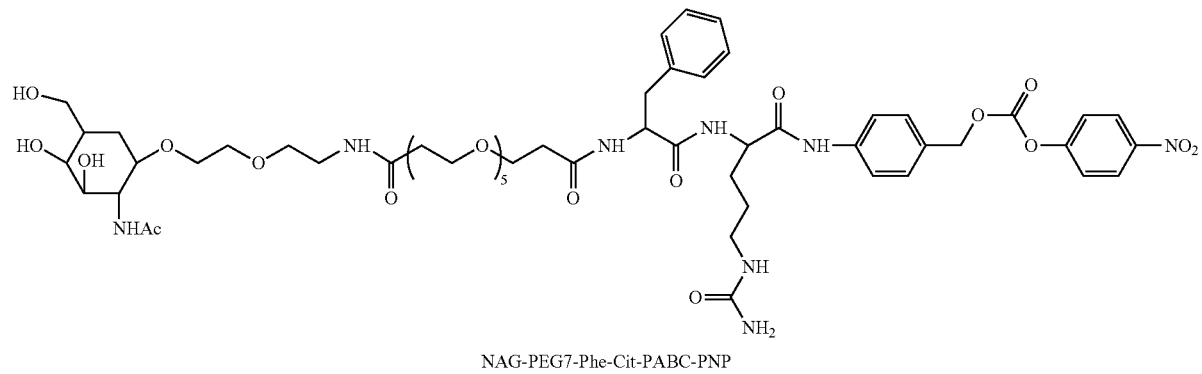
NAG-PEG7-Phe-Cit-PABC-PNP Dipeptides Glu-Gly, Ala-Cit, Phe-Cit are shown ("Cit" is the amino acid citrulline). Other amino acid combinations are permissible. In addition, 3-5 amino acids may be used as the linker between the amido benzyl group and the targeting ligand. Further, other activated carbonates known in the art are readily substituted for the para-nitrophenol used in the above compounds.

Example 4

Reversible Modification/Masking of Melittin

A. Modification with maleic anhydride-based masking agents. Prior to modification, 5× mg of disubstituted maleic anhydride masking agent (e.g. CDM-NAG) was lyophilized from a 0.1% aqueous solution of glacial acetic acid. To the dried disubstituted maleic anhydride masking agent was added a solution of × mg melittin in 0.2× mL of isotonic glucose and 10× mg of HEPES free base. Following complete dissolution of anhydride, the solution was incubated for at least 30 min at RT prior to animal administration. Reaction of disubstituted maleic anhydride masking agent with the peptide yielded:

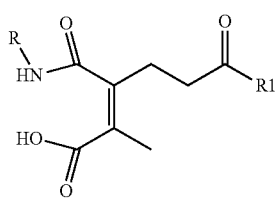

wherein R is melittin and R1 comprises a ASGPr ligand (e.g. NAG). The anhydride carboxyl produced in the reaction between the anhydride and the polymer amine exhibits ~1/20$^{th}$ of the expected charge (Rozema et al. Bioconjugate Chemistry 2003). Therefore, the membrane active polymer is effectively neutralized rather than being converted to a highly negatively charged polyanion.

B. Modification with protease cleavable masking agents. 1× mg of peptide and 10× mg HEPES base at 1-10 mg/mL peptide was masked by addition of 2-6× mg of amine-reactive p-nitrophenyl carbonate or N-hydroxysuccinimide carbonate derivatives of the NAG-containing protease cleavable substrate. The solution was then incubated at least 1 h at room temperature (RT) before injection into animals.

Example 5 siRNAs

The siRNAs had the following sequences:

```
Factor VII - rodent
                                                       (Seq ID 97)
sense: (Chol)-5' GfcAfaAfgGfcGfuGfcCfaAfcUfcAf(invdT) 3'

(Seq ID 98)
antisense: 5' pdTsGfaGfuUfgGfcAfcGfcCfuUfuGfcdTsdT 3'
or (Seq ID 99)
sense 5' GGAUfCfAUfCfUfCfAAGUfCfUfUfACfdTsdT 3'

(Seq ID 100)
antisense 5' GUfAAGACfUfUfGAGAUfGAUfCfCfdTsdT 3'

Factor VII = primate
                                                       (Seq ID 101)
Sense (chol)-5' uuAGGfuUfgGfuGfaAfuGfgAfgCfuCfaGf(invdT) 3'

(Seq ID 102)
Antisense 5' pCfsUfgAfgCfuCfcAfuUfcAfcCfaAfcdTsdT 3'

ApoB siRNA:
                                                       (Seq ID 103)
sense (cholC6SSC6)-5' GGAAUCuuAuAuuuGAUCcAsA 3'

(Seq ID 104)
antisense 5' uuGGAUcAAAuAuAAGAuUCcscsU 3' siLUC
                                                       (Seq ID 105)
sense (chol) 5'-uAuCfuUfaCfgCfuGfaGfuAfcUfuCfgAf(invdT)-3'

(Seq ID 106)
antisense 5'-UfcGfaAfgUfaCfuCfaGfcGfuAfaGfdTsdT-3'
``` lower case=2'-O—CH$_3$ substitution
s=phosphorothioate linkage
f after nucleotide=2'-F substitution
d before nucleotide=2'-deoxy RNA synthesis was performed on solid phase by conventional phosphoramidite chemistry on an ÄKTA Oligopilot 100 (GE Healthcare, Freiburg, Germany) and controlled pore glass (CPG) as solid support.

Example 6 siRNA-targeting Molecule Conjugates

A. Synthesis of GalNAc cluster. A GalNAc cluster polynucleotide targeting ligand was synthesized as described in US Patent Publication 20010207799.

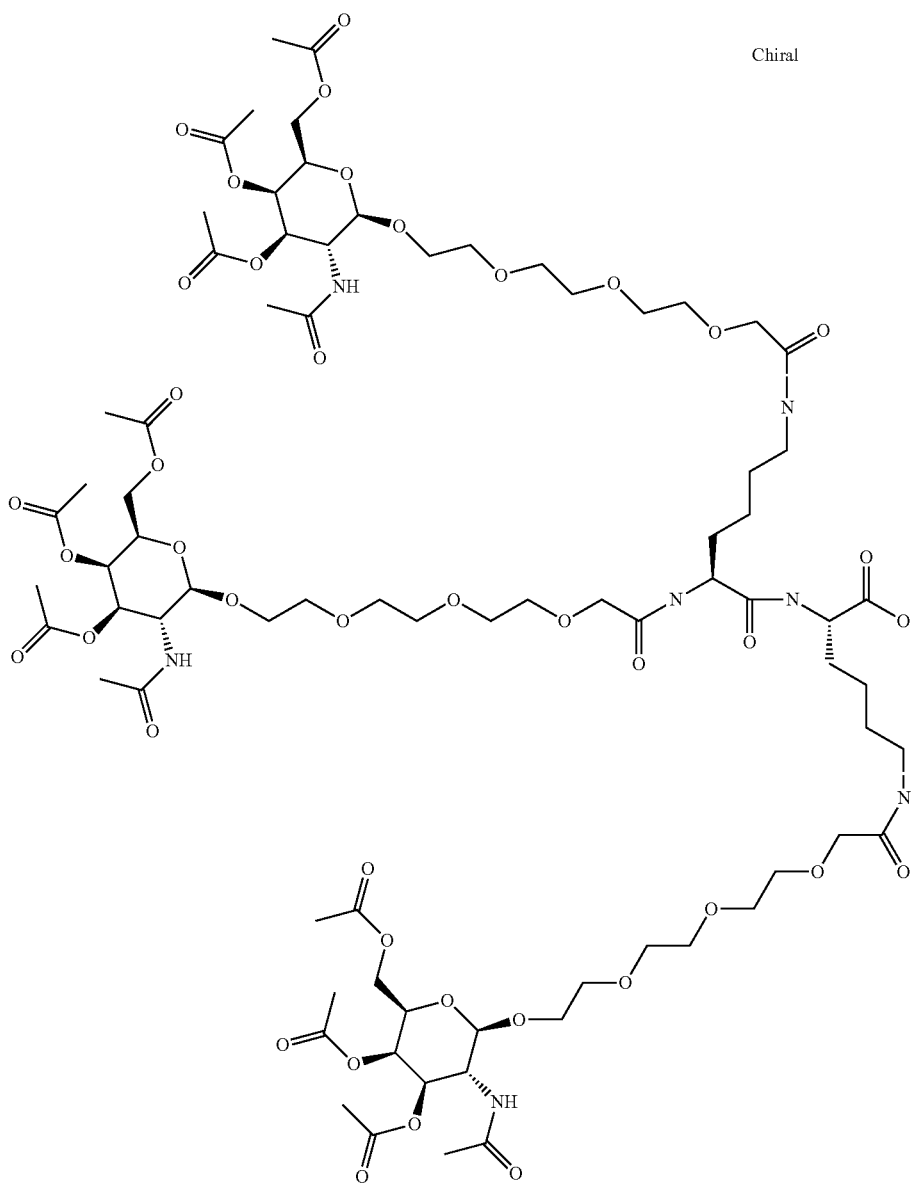 [SMILES: CC(=O)N[C@H]1[C@H](OCCOCCOCCOCC(=O)NCCCC[C@H](NC(=O)[C@H](CCCCNC(=O)COCCOCCOCCO[C@@H]2O[C@H](COC(C)=O)[C@H](OC(C)=O)[C@H](OC(C)=O)[C@H]2NC(C)=O)NC(=O)COCCOCCOCCO[C@@H]2O[C@H](COC(C)=O)[C@H](OC(C)=O)[C@H](OC(C)=O)[C@H]2NC(C)=O)C(=O)O)O[C@H](COC(C)=O)[C@H](OC(C)=O)[C@@H]1OC(C)=O]

B. GalNAc cluster-siRNA conjugates. The GalNAc cluster of Example 6A above was conjugated to siRNA as shown in FIG. 2 and as described below.

(1) Compound 1 (150 mg, 0.082 mmol, FIG. 2) was dissolved in dry methanol (5.5 ml) and 42 µL sodium methylate were added (25% solution in MeOH). The mixture was stirred under an argon atmosphere for 2 h at RT. An equal amount of methanol was added as well as portions of an anionic exchange material Amberlite IR-120 to generate a pH ~7.0. The Amberlite was removed by filtration. The solution was dried with $Na_2SO_4$, and the solvent was removed under reduced pressure. Compound 2 was obtained in quantitative yield as a white foam. TLC ($SiO_2$, dichloromethane (DCM)/MeOH 5:1+0.1% $CH_3COOH$): $R_f$ 2=0.03; for detection a solution of sulfuric acid (5%) in MeOH was used followed by heating. ESI-MS, direct injection, negative mode; $[M-H]^{-1}_{calculated}$: 1452.7; $[M-H]^{1-}_{measured}$: 1452.5.

(2) Compound 2 (20 mg, 0.014 mmol, FIG. 2) was co-evaporated with pyridine and dichloromethane. The residue was dissolved in dry DMF (0.9 ml) and a solution of N-Hydroxysuccinimide (NHS) in DMF (1.6 mg, 0.014 mmol) was added while stirring under an argon atmosphere. At 0° C. a solution of N,N'-Dicyclohexylcarbodiimide (DCC) in DMF (3.2 mg, 0.016 mmol) was slowly added. The reaction was allowed to warm to RT and stirred overnight. Compound 3 was used without further purification for conjugation to RNA.

(3) Synthesis of amino-modified RNA. RNA equipped with a C-6-amino linker at the 5'-end of the sense strand was produced by standard phosphoramidite chemistry on solid phase at a scale of 1215 µmol using an ÄKTA Oligopilot 100 (GE Healthcare, Freiburg, Germany) and controlled pore glass as solid support. RNA containing 2'-O-methyl nucleotides were generated employing the corresponding phosphoramidites, 2'-O-methyl phosphoramidites and TFA-hexylaminolinker amidite. Cleavage and deprotection as well as purification was achieved by methods known in the field (Wincott F., et al, NAR 1995, 23, 14, 2677-84).

The amino-modified RNA was characterized by anion exchange HPLC (purity: 96.1%) and identity was confirmed by ESI-MS ([M+H]$^{1+}_{calculated}$: 6937.4; [M+H]$^{1+}_{measured}$: 6939.0. Sequence: 5'-(NH$_2$C$_6$)GGAAUCuuAuAuuuGAUC-cAsA-3'; u,c: 2'-O-methyl nucleotides of corresponding bases, s: phosphorothioate.

(4) Conjugation of GalNAc Cluster to RNA. RNA (2.54 μmol) equipped with a C-6 amino linker at the 5'-end was lyophilized and dissolved in 250 μL sodium borate buffer (0.1 mol/L sodium borate, pH 8.5, 0.1 mol/L KCl) and 1.1 mL DMSO. After addition of 8 μL N,N-Diisopropylethylamine (DIPEA), a solution of compound 3 (theoretically 0.014 mmol, FIG. 2) in DMF was slowly added under continuous stirring to the RNA solution. The reaction mixture was agitated at 35° C. overnight. The reaction was monitored using RP-HPLC (Resource RPC 3 ml, buffer: A: 100 mM Triethylammonium acetate (TEAA, 2.0 M, pH 7.0) in water, B: 100 mM TEAA in 95% acetonitrile, gradient: 5% B to 22% B in 20 CV). After precipitation of RNA using sodium acetate (3 M) in EtOH at −20° C., the RNA conjugate was purified using the conditions described above. The pure fractions were pooled, and the desired conjugate compound 4 was precipitated using sodium acetate/EtOH to give the pure RNA conjugate. Conjugate 4 has been isolated in 59% yield (1.50 μmol). The purity of conjugate 4 was analyzed by anion exchange HPLC (purity: 85.5%) and identity was confirmed by ESI-MS ([M+H]$^{1+}_{calculated}$: 8374.4; [M+H]$^{1+}_{measured}$: 8376.0.

(5) Conjugate 4 (sense strand) was annealed with an 2'-O-methyl-modified antisense Strand. The siRNA conjugate was generated by mixing an equimolar solution of complementary strands in annealing buffer (20 mM sodium phosphate, pH 6.8; 100 mM sodium chloride), heated in a water bath at 85-90° C. for 3 min, and cooled to RT over a period of 3-4 h. Duplex formation was confirmed by native gel electrophoresis.

C. Hydrophobic group-siRNA conjugates. (1) siRNA conjugation to alkyl groups. A 5'-C10-NHS ester modified sense strand of siRNA (NHSC10-siRNA, or COC9-siRNA) was prepared employing 5'-Carboxy-Modifier C10 amidite from Glen Research (Virginia, USA). The activated RNA, still attached to the solid support was used for conjugation with lipophilic amines listed in Table 1 below. 100 mg of the sense strand CPG (loading 60 μmol/g, 0.6 μmol RNA) were mixed with 0.25 mmol of the corresponding amine obtained from, Sigma Aldrich Chemie GmbH (Taufkirchen, Germany) or Fluka (Sigma-Aldrich, Buchs, Switzerland).

TABLE 1

Lipophilic amines used in forming hydrophobic group-siRNA conjugates

| Nr | Lipophilic Amine | mg | mmol | solvent |
|---|---|---|---|---|
| 2 | N-Hexylamine | 25 | 0.25 | 1 mL CH$_2$Cl$_2$ |
| 3 | Dodecylamine | 50 | 0.25 | 0.55 mL CH$_3$CN, 0.45 mL CH$_2$Cl$_2$ |
| 4 | Octadecylamine | 67 | 0.25 | 1 mL CH$_2$Cl$_2$ |
| 5 | Didecylamine | 74 | 0.25 | 1 mL CH$_2$Cl$_2$ |
| 6 | Didodecylamine | 88 | 0.25 | 1 mL CH$_2$Cl$_2$ |
| 7 | Dioctadecylamine | 67 | 0.12 | 0.45 mL CH$_2$Cl$_2$, 0.45 mL Cyclohexan |

The mixture was shaken for 18 h at 40° C. The RNA was cleaved from the solid support and deprotected with an aqueous ammonium hydroxide solution (NH$_3$, 33%) at 45° C. overnight. The 2'-protecting group was removed with TEA×3HF at 65° C. for 3.5 h. The crude oligoribonucleotides were purified by RP-HPLC (Resource RPC 3 ml, buffer: A: 100 mM TEAA in water, B: 100 mM TEAA in 95% CH$_3$CN, gradient: 3% B to 70% B in 15 CV, except for Nr 7: gradient from 3% B to 100% B in 15 CV).

To generate siRNA from RNA single strand, equimolar amounts of complementary sense and antisense strands were mixed in annealing buffer (20 mM sodium phosphate, pH 6.8; 100 mM sodium chloride), heated at 80° C. for 3 min, and cooled to RT over a period of 3-4 h. The siRNA, which are directed against factor VII mRNA were characterized by gel electrophoresis.

(2) siRNA conjugation to cholesterol—siRNA-cholesterol conjugates were synthesized using methods standard in the art. Cholesterol can be attached to the 5' or 3' termini of the sense or antisense strand of the siRNA. A preferred attachment is to the 5' end of the sense strand of the siRNA. siRNA-Cholesterol can also be made post siRNA synthesis using RNA strands containing a reactive group (e.g. thiol, amine, or carboxyl) using methods standard in the art.

In Vivo siRNA Delivery

Example 7

Administration of RNAi Polynucleotides In Vivo, and Delivery to Hepatocytes

RNAi polynucleotide conjugates and masked melittin peptides were synthesized as described above. Six to eight week old mice (strain C57BL/6 or ICR, ~18-20 g each) were obtained from Harlan Sprague Dawley (Indianapolis Ind.). Mice were housed at least 2 days prior to injection. Feeding was performed ad libitum with Harlan Teklad Rodent Diet (Harlan, Madison Wis.). Mice were injected with 0.2 mL solution of delivery peptide and 0.2 mL siRNA conjugates into the tail vein. For simultaneous injection of delivery peptide and siRNA, the siRNA-conjugate was added to modified peptide prior to injection and the entire amount was injected. The composition was soluble and nonaggregating in physiological conditions. Solutions were injected by infusion into the tail vein. Injection into other vessels, e.g. retro-orbital injection, are predicted to be equally effective.

Wistar Han rats, 175-200 g were obtained from Charles River (Wilmington, Mass.). Rats were housed at least 1 week prior to injection. Injection volume for rats was typically 1 ml.

Serum ApoB levels determination. Mice were fasted for 4 h (16 h for rats) before serum collection by submandibular bleeding. For rats blood was collected from the jugular vein. Serum ApoB protein levels were determined by standard sandwich ELISA methods. Briefly, a polyclonal goat anti-mouse ApoB antibody and a rabbit anti-mouse ApoB antibody (Biodesign International) were used as capture and detection antibodies respectively. An HRP-conjugated goat anti-rabbit IgG antibody (Sigma) was applied afterwards to bind the ApoB/antibody complex. Absorbance of tetramethyl-benzidine (TMB, Sigma) colorimetric development was then measured by a Tecan Safire2 (Austria, Europe) microplate reader at 450 nm.

Plasma Factor VII (F7) activity measurements. Plasma samples from animals were prepared by collecting blood (9 volumes) (by submandibular bleeding for mice or from jugular vein for rats) into microcentrifuge tubes containing 0.109 mol/L sodium citrate anticoagulant (1 volume) following standard procedures. F7 activity in plasma is measured with a chromogenic method using a BIOPHEN VII kit (Hyphen BioMed/Aniara, Mason, Ohio) following manufacturer's recommendations. Absorbance of colorimetric development was measured using a Tecan Safire2 microplate reader at 405 nm.

Example 8

In vivo Knockdown of Endogenous ApoB Levels Following Delivery of ApoB siRNA with Melittin Delivery Peptide—does Response of Melittin Peptide Melittin was reversibly modified with CDM-NAG as described above. The indicated amount of melittin was then co-injected with the 200 µg ApoB siRNA-cholesterol conjugate. Effect on ApoB levels were determined as described above.

TABLE 2

Inhibition of ApoB activity in normal liver cells in mice treated with ApoB-siRNA-cholesterol conjugate and CDM-NAG vs. CDM-PEG reversibly inhibited Melittin peptide.

| Peptide Name | Modification | µg siRNA | µg peptide | % knockdown[a] |
|---|---|---|---|---|
| Apis florea (Seq ID 1) L form | 5× CDM-PEG | 200 | 800 | 0 |
| | | 200 | 100 | 25 |
| | | 200 | 200 | 51 |
| | 5× CDM-NAG | 200 | 400 | 78 |
| | | 200 | 800 | 87 |
| | | 200 | 1200 | 94 |

[a]Knockdown relative to isotonic glucose injected animals

Example 9

In vivo Knockdown of Endogenous Factor VII Levels Following Delivery of ApoB siRNA with Melittin Delivery Peptide in Rats The indicated melittin was reversibly modified with 5×CDM-NAG as described above. The indicated amount of melittin, in mg per kg animal weight, was then co-injected with the 3 mg/kg cholesterol—Factor VII siRNA. Effect on Factor VII levels were determined as described above.

TABLE 3

Inhibition of Factor VII activity in normal liver cells in rats treated with Factor VII-siRNA-cholesterol conjugate and CDM-NAG reversibly inhibited melittin.

| Seq ID | Peptide | µg peptide[a] | Factor VII knockdown[b] |
|---|---|---|---|
| 1 | GIGAILKVLATGLPTLISWIKNKRKQ | 1 | 30 |
| | | 3 | 83 |
| | | 10 | 90 |
| | | 20 | 95 |

TABLE 3-continued

Inhibition of Factor VII activity in normal liver cells in rats treated with Factor VII-siRNA-cholesterol conjugate and CDM-NAG reversibly inhibited melittin.

| Seq ID | Peptide | µg peptide[a] | Factor VII knockdown[b] |
|---|---|---|---|
| 11 | YIGAILKVLATGLPTLISWIKNKRKQ | 1 | 93 |
| | | 3 | 97 |

[a]mg peptide per kilogram animal weight
[b]Knockdown relative to isotonic glucose injected animals

Example 10

In vivo Knockdown of Endogenous ApoB Levels Following Delivery of ApoB siRNA With Melittin Delivery Peptide in Mice, L-Form Vs. D-Form Melittin Melittin was Reversibly modified with CDM-NAG as described above. The indicated amount of melittin was then co-injected with 50 µg ApoB siRNA-cholesterol conjugate. Effect on ApoB levels were determined as described above.

TABLE 4

Inhibition of ApoB activity in normal liver cells in mice treated with ApoB-siRNA cholesterol conjugate and the indicated CDM-NAG reversibly inhibited melittin peptide.

| Peptide Name | Modification | µg siRNA | µg peptide | % knockdown |
|---|---|---|---|---|
| Leu-Melittin (Seq ID 7) L form | 5× CDM-NAG | 50 | 25 | 15 |
| | | 50 | 50 | 70 |
| | | 50 | 100 | 90 |
| | | 50 | 200 | 90 |
| | | 50 | 400 | 90 |
| Leu-Melittin (Seq ID 7) D form | 5× CDM-NAG | 50 | 25 | 30 |
| | | 50 | 50 | 80 |
| | | 50 | 100 | 90 |

Example 11

In vivo Knockdown of Endogenous ApoB Levels Following Delivery of ApoB siRNA with Melittin Delivery Peptide in Mice, Normal Vs. Reversed (Retro) Sequence Melittin was reversibly modified with CDM-NAG (5×) as described above. The indicated amount of melittin was then co-injected with the indicated amount of ApoB siRNA-cholesterol conjugate. Effect on ApoB levels were determined as described above.

TABLE 5

Inhibition of ApoB activity in normal liver cells in mice treated with ApoB-siRNA cholesterol conjugate and the indicated CDM-NAG reversibly inhibited Melittin peptide.

| Seq ID | modification | Peptide | siRNA | percent knockdown |
|---|---|---|---|---|
| 1 | | GIGAILKVLATGLPTLISWIKNKRKQ | 200 µg | 90 |
| | | | 400 µg | 80 |
| 95 | Retroinverso[a] Methoxy | QQRKRKIWSILAALGTTLVKLVAGIC-NH$_2$ | 30 mg/kg | 39 |

TABLE 5-continued

Inhibition of ApoB activity in normal liver cells in mice treated with ApoB-siRNA cholesterol conjugate and the indicated CDM-NAG reversibly inhibited Melittin peptide.

| Seq ID | modification | Peptide | siRNA | percent knockdown |
|---|---|---|---|---|
| 92 | retroinverso | QQRKRKIWSILAPLGTTLVKLVAGIC-NH$_2$ | 400 µg | 85 |
|  |  |  | 20 mg/kg | 94 |
| 95 | retroinverso | QQRKRKIWSILAALGTTLVKLVAGIC-NH$_2$ | 20 mg/kg | 91 |
| 93 | retroinverso | QQKKKKIWSILAPLGTTLVKLVAGIC-NH$_2$ | 20 mg/kg | 70 |
| 96 | retroinverso | QKRKNKIWSILTPLGTALVKLIAGIG-NH$_2$ | 20 mg/kg | 70 |

$^a$-retroinverso = normal melittin amino acid sequence is reversed and all amino acids are D-form amino acids (Glycine (G) is achiral)

Example 12

In vivo Knockdown of Endogenous ApoB Levels Following Delivery of ApoB siRNA with Melittin Delivery Peptide in Mice, Melittin Modification Level Melittin was Reversibly modified with the indicated amount of CDM-NAG as described above. 50 µg melittin was then co-injected with the 100 µg ApoB siRNA-cholesterol conjugate. Effect on ApoB levels were determined as described above.

Percent melittin amine modification was determined by TNBS Assay for free amines on the peptide. 20 µg peptide was pipetted into 96 well clear plate (NUNC 96) containing 190 µL 50 mM BORAX buffer (pH 9) and 16 µg TNBS. Sample were allowed to react with TNBS for ~15 minutes at RT and then the A$_{420}$ is measured on a Safire plate reader. Calculate the % amines modified as follows: (A$_{control}$−A$_{sample}$)/(A$_{control}$−A$_{blank}$)×100. Modification of more than 80% of amines provided optimal melittin masking and activity.

TABLE 6

Inhibition of ApoB activity in normal liver cells in mice treated with ApoB-siRNA cholesterol conjugate and Melittin reversibly modified at the indicated levels with CDM-NAG.

| Peptide Name | Modification | µg siRNA | µg peptide | % amines modified $^a$ | % knock-down |
|---|---|---|---|---|---|
| Leu-Melittin | 1× CDM-NAG | 100 | 50 | 68 | 74 |
| (Seq ID 7) | 2× CDM-NAG | 100 | 50 | 88 | 88 |
| L form | 5× CDM-NAG | 100 | 50 | 98 | 82 |

$^a$ determined by TNBS assay

Example 13

In vivo Knockdown of Endogenous ApoB Levels Following Delivery of ApoB siRNA with Melittin Delivery Peptide in Mice, Melittin Peptide Derivatives Melittin peptides having the indicated sequence were reversibly modified with CDM-NAG (5×) as described above. The indicated amount of melittin was then co-injected with the indicated amount of ApoB siRNA-cholesterol conjugate. Effect on ApoB levels were determined as described above.

TABLE 7

Inhibition of ApoB activity in normal liver cells in mice treated with ApoB-siRNA cholesterol conjugate and the indicated CDM-NAG reversibly inhibited Melittin peptide.

| Peptide Name | µg peptide$^a$ | µg siRNA$^b$ | percent knockdown |
|---|---|---|---|
| CBZ-Mel (Seq ID 1) | 100 | 80 | 96 |
| Mel-NH$_2$ (Seq ID 1) | 50 | 100 | 86 |
| Acetyl-dMel-NH$_2$ (Seq ID 1) | 100 | 100 | 89 |
| G1A (Seq ID 2) | 100 | 100 | 88 |
| G1C (Seq ID 3) | 100 | 100 | 37 |
| G1F dMel (Seq ID 4) | 100 | 50 | 94 |
| G1H (Seq ID 5) | 400 | 100 | 78 |
| G1dI (D form Ile at 1$^{st}$ position, Seq ID 6) | 50 | 100 | 34 |
| G1L d-Mel (Seq ID 7) | 50 | 100 | 91 |

TABLE 7-continued

Inhibition of ApoB activity in normal liver cells in mice treated with ApoB-siRNA cholesterol conjugate and the indicated CDM-NAG reversibly inhibited Melittin peptide.

| Peptide Name | μg peptide[a] | μg siRNA[b] | percent knockdown |
|---|---|---|---|
| G1L d(1-11)-l(12-26) (Seq ID 7) | 100 | 100 | 70 |
| G1Nle (Seq ID 8) | 100 | 100 | 96 |
| G1V (Seq ID 9) | 100 | 100 | 91 |
| G1W (Seq ID 10) | 200 | 200 | 96 |
| G1Y dMel (Seq ID 11) | 100 | 50 | 95 |
| G1Y-Mel-NH$_2$ (Seq ID 11) | 200 | 200 | 94 |
| G12L (Seq ID 13) | 80 | 100 | 58 |
| G12W (Seq ID 14) | 80 | 100 | 51 |
| N22T Mel-NH$_2$ (Seq ID 15) | 50 | 100 | 34 |
| G1Y, K7N (Seq ID 16) | 80 | 100 | 32 |
| G1Y, K7A (Seq ID 17) | 400 | 100 | 83 |
| G1L, K7S (Seq ID 18) | 100 | 100 | 89 |
| G1L, K7R (Seq ID 19) | 100 | 100 | 92 |
| G1L, K7H (Seq ID 20) | 100 | 100 | 97 |
| G1L, T11C dMel (Seq ID 21) | 100 | 50 | 81 |
| G1L, G12L (Seq ID 22) | 400 | 100 | 93 |
| G1L, T15C dMel (Seq ID 24) | 100 | 100 | 95 |
| G1L, S18C (Seq ID 25) | 100 | 100 | 93 |
| G1L, K21A (Seq ID 28) | 100 | 100 | 95 |
| G1Y, K23A (Seq ID 29) | 100 | 100 | 42 |
| G1L, R24A (Seq ID 30) | 100 | 100 | 87 |
| G1Y, K25A (Seq ID 31) | 100 | 100 | 77 |
| G1Y, Q26C (Seq ID 32) | 100 | 100 | 93 |
| G1Y, K7A, K21A (Seq ID 35) | 100 | 100 | 14 |
| G1L, T11C, S18C dMel (Seq ID 38) | 100 | 100 | 88 |
| T11G, T15G, S18G (Seq ID 39) | 50 | 100 | 32 |
| T11A, T15A, S18A (Seq ID 40) | 50 | 100 | 38 |
| G1L, I2L, I5L, I17L, I20L (Seq ID 43) | 400 | 100 | 96 |
| G1L, I2Nle, I5Nle, I17Nle, I20Nle (Seq ID 44) | 100 | 100 | 99 |
| G1L, I2V, I5V, I17V, I20V (Seq ID 45) | 100 | 100 | 24 |
| dimethyl-dMel I2L, I5L, T11C, I17L, I20L dMel (Seq ID 46) | 100 | 100 | 87 |
| dimethyl-dMel I2Nle, I5Nle, T11C, I17Nle, I20Nle dMel (Seq ID 47) | 100 | 100 | 78 |
| *Apis Mellifera* (Big Honey Bee; Seq ID 50) | 400 | 100 | 72 |
| C-Mel G1L (Seq ID 51) | 100 | 100 | 89 |
| C-dMel G1Nle (Seq ID 52) | 100 | 100 | 84 |
| Dimethyl G-Mel G1L (Seq ID 53) | 100 | 100 | 91 |

TABLE 7-continued

Inhibition of ApoB activity in normal liver cells in mice treated with ApoB-siRNA cholesterol conjugate and the indicated CDM-NAG reversibly inhibited Melittin peptide.

| Peptide Name | μg peptide[a] | μg siRNA[b] | percent knockdown |
|---|---|---|---|
| PEG(5k)-KLK-dMel G1Y (Seq ID 56) | 300 | 100 | 72 |
| CKLK-Mel G1L (Seq ID 57) | 150 | 100 | 91 |
| myristoyl-CKLK-Mel G1L (Seq ID 57) | 80 | 100 | 96 |
| CKLK-dMel G1Nle (Seq ID 58) | 200 | 100 | 84 |
| Acetyl-CKLK-dMel G1Nle (Seq ID 58) | 100 | 200 | 97 |
| PEG24-GKLK-Mel G1L (Seq ID 59) | 50 | 100 | 85 |
| Mel-Cys (Seq ID 62) | 400 | 100 | 83 |
| G1L Mel-Cys (Seq ID 63) | 400 | 100 | 82 |
| G1L dMel-C (Seq ID 63) | 50 | 100 | 93 |
| G1Nle Mel-C (Seq ID 64) | 400 | 50 | 89 |
| G1L Mel-KLKC (Seq ID 65) | 100 | 100 | 97 |
| G1Y Mel-PLGIAGQC (Seq ID 66) | 100 | 100 | 79 |
| G1L, Mel-KKKKK (Seq ID 67) | 400 | 100 | 96 |
| G1Y dMel-GFKGC (Seq ID 68) | 400 | 100 | 96 |
| CFK-G1L dMel-C (Seq ID 69) | 100 | 100 | 79 |
| G1L Mel (1-23) (Seq ID 71) | 400 | 100 | 69 |
| G1L, L5V, A10T, T15A Mel (1-23) (Seq ID 72) | 400 | 100 | 69 |
| G1L, L5V, A10T, T15A, N22G, K23E dMel (1-23) (Seq ID 73) | 400 | 100 | 92 |
| G1L retroMel-KLK-Stearoyl (Seq ID 75) | 400 | 100 | 50 |
| G1L retroMel-Stearoyl (Seq ID 74) | 400 | 100 | 56 |
| G1L retro-dMel-KLK-PEG(5k) (Seq ID 75) | 100 | 100 | 32 |
| QQRKRKIWSILAPLGTTLVKLVAGIC-(N-PDP-PE)-NH$_2$ dMel (Seq ID 92) (PE = dioleolyl-phosphatidyl-ethanolamine) | 400 | 200 | 55 |
| Ac-CIGAVLKVLTTGLPALISWIKRKRQQ-NH2 (Seq ID 90) | 400 | 200 | 85 |
| (Ac-CIGAVLKVLTTGLPALISWIKRKRQQ-NH$_2$)$_2$ (Seq ID 90) | 400 | 200 | 45 |

[a] μg peptide per mouse
[b] μg siRNA per mouse
dMel = Melittin peptide having D-form amino acids

Example 14

In vivo Knockdown of Endogenous ApoB Levels Following Delivery of ApoB siRNA with Melittin Delivery Peptide in Mice, Enzymatically Cleavable Masking Agents Melittin was reversibly modified with the indicated amount of enzymatically cleavable masking agents as described above. 200-300 μg masked melittin was then co-injected with the 50-100 μg ApoB siRNA-cholesterol conjugate. Effect on ApoB levels were determined as described above. Peptidase cleavable dipeptide-amidobenzyl carbamate modified melittin was an effective siRNA delivery peptide. The use of D-from melittin peptide is preferred in combination with the enzymatically cleavable masking agents. While more peptide was required for the same level of target gene knockdown, because the peptide masking was more stable, the therapeutic index was either not altered or improved (compared to masking of the same peptide with CDM-NAG).

TABLE 8

Inhibition of Factor VII activity in normal liver cells in mice treated with Factor VII-siRNA cholesterol conjugate and G1L-Melittin (D form) (Seq ID 7) reversibly inhibited with the indicated enzymatically cleavable masking agent.

| Peptide | amount[a] | NAG-linkage type | µg peptide | µg siRNA | percent knock-down |
|---|---|---|---|---|---|
| G1L d-Mel (Seq ID 7) | 5× | CDM-NAG | 200 | 100 | 97 |
| | 5× | NAG-AlaCit | 200 | 50 | 96 |
| | 5× | NAG-GluGly | 200 | 50 | 96 |
| | 5× | NAG-PEG$_4$-PheCit | 200 | 50 | 94 |
| | 5× | NAG-PEG$_7$-PheCit | 200 | 50 | 86 |
| | 5× | CDM-NAG | 300 | 50 | 98 |
| | 2× | NAG-GluGly | 300 | 50 | 95 |
| | 4× | NAG-GluGly | 300 | 50 | 95 |
| | 6× | NAG-GluGly | 300 | 50 | 82 |

[a]Amount of masking agent per Melittin amine used in the masking reaction.

Example 15

In vivo Knockdown of Endogenous ApoB Levels Following Delivery of ApoB siRNA with Melittin Delivery Peptide in Mice, Amine Modified Melittin Peptides Melittin peptides containing the indicated PEG amino terminal modifications were synthesized as described above. The PEG amino terminal modified melittin peptides were then reversibly modified with 5×CDM-NAG as described above. The indicated amount of Melittin was then co-injected with the 100-200 µg ApoB siRNA-cholesterol conjugate. Effect on ApoB levels were determined as described above. Addition of PEG less than 5 kDa in size decreased toxicity of the melittin peptides. Amino terminal modification with PEG greater than 5 kDa resulted in decreased efficacy (data not shown).

TABLE 9

Inhibition of ApoB activity in normal liver cells in mice treated with ApoB-siRNA cholesterol conjugate and the indicated CDM-NAG reversibly inhibited Melittin peptide.

| Peptide | NAG amount | PEG | µg peptide | µg siRNA | percent knock-down |
|---|---|---|---|---|---|
| G1L (Seq ID 7) | 5× | | 25 | 100 | 0 |
| | | | 50 | 100 | 72 |
| | | | 100 | 100 | 94 |
| CKLK-Mel G1L (Seq ID 57) | 5× | | 150 | 100 | 91 |
| | | | 400 | 100 | 97 |
| | 5× | NAG-(PEG)2 | 25 | 100 | 15 |
| | | | 50 | 100 | 83 |
| | 5× | NAG-(PEG)4 | 25 | 100 | 58 |
| | | | 50 | 100 | 81 |
| | | | 100 | 100 | 94 |
| | 5× | NAG-(PEG)8 | 25 | 100 | 58 |
| | | | 50 | 100 | 89 |
| | | | 100 | 100 | 96 |
| Acetyl-CKLK-dMel G1Nle (Seq ID 58) | 5× | | 100 | 200 | 90 |
| | | | 200 | 100 | 90 |
| | | PEG (1k) | 150 | 100 | 93 |
| CRLR-Mel | 5× | PEG (1k) | 100 | 100 | 93 |
| CKFR-Mel | 5× | PEG (1k) | 100 | 100 | 81 |
| CKLK-Mel G1L (Seq ID 57) | 5× | PEG (5k) | 100 | 100 | 90 |

Example 16

Other Melittin Derivative Sequences Known to have Membrane Activity

TABLE 10

Melittin peptides having membrane activity.

| Seq ID | Sequence | Peptide Name |
|---|---|---|
| 76 | GIGAVLKVLTTGLPALISWISRKKRQQ | I5V, A10T, T15A, N22R, R24K, K25R Mel-Q |
| 77 | GIGARLKVLTTGLPR ISWIKRKRQQ | I5R, A10T, T15R, L16Δ, N22R, K25Q |
| 78 | GIGAILKVLSTGLPALISWIKRKRQE | A10S, T15A, N22R, K25Q, Q26E |
| 79 | GIGAVLKVLTTGLPALIGWIKRKRQQ | I5V, A10T, T15A, S18G, N22R, K25Q |
| 80 | GIGAVLKVLATGLPALISWIKRKRQQ | I5V, T15A, N22R, K25Q |
| 81 | GIGAVLKVLSTGLPALISWIKRKRQQ | I5V, A10S, T15A, N22R, K25Q |
| 82 | GIGAILRVLATGLPTLISWIKNKRKQ | K7R |
| 83 | GIGAILKVLATGLPTLISWIKRKRKQ | N22R |
| 84 | GIGAILKVLATGLPTLISWIKKKQQ | N22K, R24K, K25Q |
| 85 | GIGAILKVLATGLPTLISWIKNKRKQGSKKKK | Mel-GSKKKK |
| 86 | KKGIGAILKVLATGLPTLISWIKNKRKQ | KK-Mel |
| 87 | GIGAILEVLATGLPTLISWIKNKRKQ | K7E Mel |
| 88 | GIGAVLKVLTTGLPALISWIKRKR | I5V, T15A, N22R, 25-26Δ |
| 89 | GIGAVLKVLTTGLPALISWIKR | I5V, T15A, N22R, 23-26Δ |
| 94 | QKRKNKIWSILTPLGTALVKLIAGIG-NH$_2$ | Q25K reverse Mel |

Example 17

Figure 5:
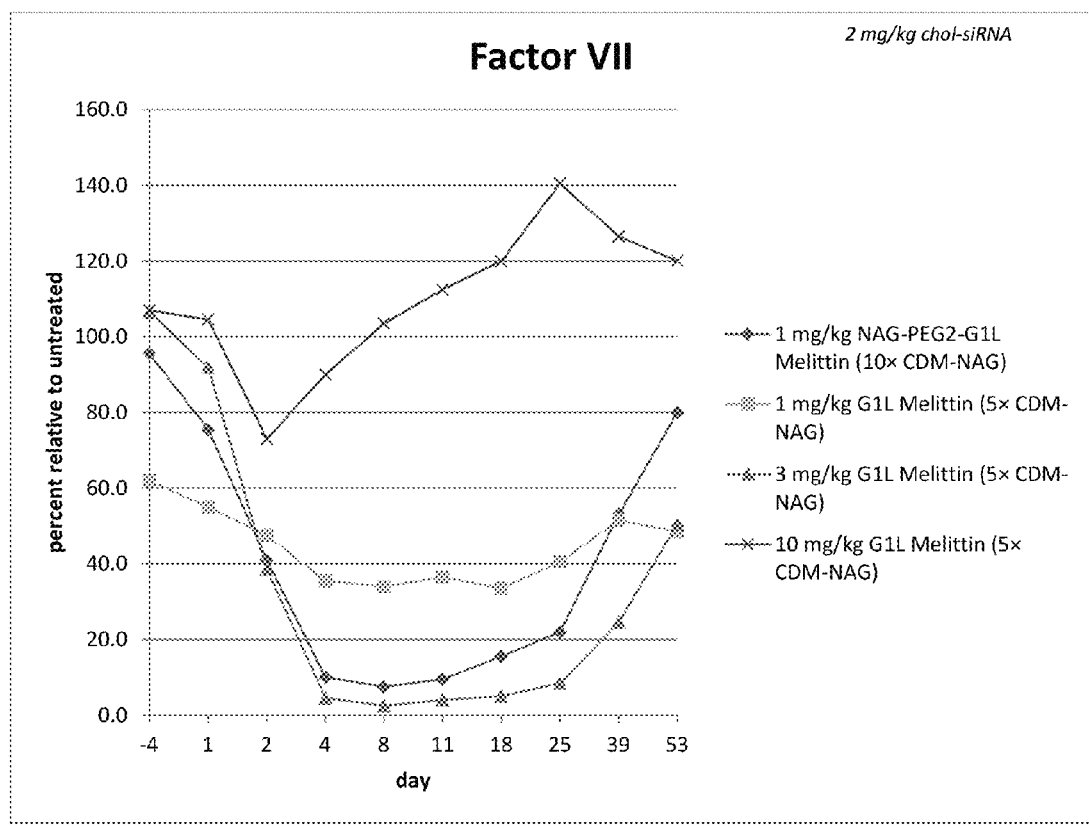
FIG. 5. Graph illustrating knockdown of endogenous Factor VII levels in primates treated with reversibly modified melittin siRNA delivery peptides and siRNA-cholesterol conjugates.

Factor VII Knockdown in Primate Following Factor VII siRNA Delivery by Melittin Delivery Peptide NAG-PEG2-G1L melittin was masked by reaction with 10×CDM-NAG as described above. GIL melittin was masked by reaction with 5×CDM-NAG as described above. On day 1, 1 mg/kg masked NAG-PEG2-G1L melittin, 1 mg/kg masked GIL melittin, or 3 mg/kg masked GIL melittin were co-injected with 2 mg/kg chol-Factor VII siRNA into Cynomolgus macaque (*Macaca fascicularis*) primates (male, 3.0 to 8.0 kg). 2 ml/kg was injected into the saphenous vein using a 22 to 25 gauge intravenous catheter. As a control, another set of primates were co-injected with 10 mg/kg GIL melittin and 2 mg/kg of a control siRNA, chol-Luciferasr siRNA. At the indicated time points (indicated in FIG. 3-5), blood samples were drawn and analyzed for Factor VII and toxicity markers. Blood was collected from the femoral vein and primates are fasted overnight before all blood collections. Blood tests for blood urea nitrogen (BUN), alanine transaminase (ALT), aspartate aminotransferase (AST), and creatinine were performed on a Cobas Integra 400 (Roche Diagnostics) according to the manufacturer's recommendations. Factor VII levels were determined as described above. Significant knockdown of Factor VII was observed at less than 1 mg/kg peptide dose. No significant toxicity was observed at a dose of 10 mg/kg peptide. Thus, the masked melittin peptides have a therapeutic index of 5-10.

Example 18

ApoB Knockdown in Primate Following ApoB siRNA Delivery by Melittin Delivery Peptide GIL melittin was masked by reaction with 5×CDM-NAG as described above. On day 1, 2 mg/kg masked GIL melittin was co-injected with 2 mg/kg chol-ApoB siRNA into Cynomolgus macaque (*Macaca fascicularis*) primates. At the indicated time points (Table 11), blood samples were drawn and analyzed for ApoB protein levels and toxicity markers. Blood tests for blood urea nitrogen (BUN), alanine transaminase (ALT), aspartate aminotransferase (AST), and creatinine were performed on a Cobas Integra 400 (Roche Diagnostics) according to the manufacturer's recommendations. ApoB levels were determined as described above. No increases in BUN, Creatinine, or AST were observed. Only a transient, minor elevation in AST was observed on day 2 (1 day after injection). Knockdown of ApoB reached nearly 100% at day 11 and remained low for 31 days.

TABLE 11

Inhibition of ApoB activity in normal liver cells in primate treated with ApoB-siRNA cholesterol conjugate and CDM-NAG masked G1L melittin.

| | day | | | | | | | | | |
|---|---|---|---|---|---|---|---|---|---|---|
| | 4 | 1 | 2 | 4 | 8 | 11 | 15 | 18 | 25 | 31 |
| BUN (mg/dl) | 21 | 26 | 22 | 23 | 27 | 27 | 28 | 22 | 22 | 22 |
| Creatinine (mg/dl) | 0.8 | 0.9 | 0.9 | 0.7 | 0.8 | 0.8 | 0.9 | 0.9 | 0.9 | 0.9 |
| AST (U/L) | 25 | 27 | 71 | 30 | 37 | 27 | 32 | 29 | 39 | 50 |
| ALT (U/L) | 34 | 33 | 58 | 49 | 50 | 46 | 46 | 41 | 39 | 44 |
| apoB (mg/dl) | 1072 | 1234 | 198 | 23 | 4 | 0 | 34 | 43 | 76 | 184 |

The invention claimed is:
1. A reversibly masked melittin peptide having the structure represented by
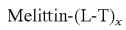
wherein Melittin is a melittin peptide, L is a physiologically lab

SEQUENCE LISTING

<160> NUMBER OF SEQ ID NOS: 106

<210> SEQ ID NO 1
<211> LENGTH: 26
<212> TYPE: PRT
<213> ORGANISM: Apis florea

<400> SEQUENCE: 1

Gly Ile Gly Ala Ile Leu Lys Val Leu Ala Thr Gly Leu Pro Thr Leu
1               5                   10                  15

Ile Ser Trp Ile Lys Asn Lys Arg Lys Gln
            20                  25

<210> SEQ ID NO 2
<211> LENGTH: 26
<212> TYPE: PRT
<213> ORGANISM: Apis florea

<400> SEQUENCE: 2

Ala Ile Gly Ala Ile Leu Lys Val Leu Ala Thr Gly Leu Pro Thr Leu
1               5                   10                  15

Ile Ser Trp Ile Lys Asn Lys Arg Lys Gln
            20                  25

<210> SEQ ID NO 3
<211> LENGTH: 26
<212> TYPE: PRT
<213> ORGANISM: Apis florea

<400> SEQUENCE: 3

Cys Ile Gly Ala Ile Leu Lys Val Leu Ala Thr Gly Leu Pro Thr Leu
1               5                   10                  15

```
Ile Ser Trp Ile Lys Asn Lys Arg Lys Gln
            20                  25
```

```
<210> SEQ ID NO 4
<211> LENGTH: 26
<212> TYPE: PRT
<213> ORGANISM: Apis florea

<400> SEQUENCE: 4

Phe Ile Gly Ala Ile Leu Lys Val Leu Ala Thr Gly Leu Pro Thr Leu
1               5                   10                  15

Ile Ser Trp Ile Lys Asn Lys Arg Lys Gln
            20                  25
```

```
<210> SEQ ID NO 5
<211> LENGTH: 26
<212> TYPE: PRT
<213> ORGANISM: Apis florea

<400> SEQUENCE: 5

His Ile Gly Ala Ile Leu Lys Val Leu Ala Thr Gly Leu Pro Thr Leu
1               5                   10                  15

Ile Ser Trp Ile Lys Asn Lys Arg Lys Gln
            20                  25
```

```
<210> SEQ ID NO 6
<211> LENGTH: 26
<212> TYPE: PRT
<213> ORGANISM: Apis florea

<400> SEQUENCE: 6

Ile Ile Gly Ala Ile Leu Lys Val Leu Ala Thr Gly Leu Pro Thr Leu
1               5                   10                  15

Ile Ser Trp Ile Lys Asn Lys Arg Lys Gln
            20                  25
```

```
<210> SEQ ID NO 7
<211> LENGTH: 26
<212> TYPE: PRT
<213> ORGANISM: Apis florea

<400> SEQUENCE: 7

Leu Ile Gly Ala Ile Leu Lys Val Leu Ala Thr Gly Leu Pro Thr Leu
1               5                   10                  15

Ile Ser Trp Ile Lys Asn Lys Arg Lys Gln
            20                  25
```

```
<210> SEQ ID NO 8
<211> LENGTH: 28
<212> TYPE: PRT
<213> ORGANISM: Apis florea

<400> SEQUENCE: 8

Asn Leu Glu Ile Gly Ala Ile Leu Lys Val Leu Ala Thr Gly Leu Pro
1               5                   10                  15

Thr Leu Ile Ser Trp Ile Lys Asn Lys Arg Lys Gln
            20                  25
```

```
<210> SEQ ID NO 9
<211> LENGTH: 26
<212> TYPE: PRT
<213> ORGANISM: Apis florea
```

<400> SEQUENCE: 9

Val Ile Gly Ala Ile Leu Lys Val Leu Ala Thr Gly Leu Pro Thr Leu
1               5                   10                  15

Ile Ser Trp Ile Lys Asn Lys Arg Lys Gln
            20                  25

<210> SEQ ID NO 10
<211> LENGTH: 26
<212> TYPE: PRT
<213> ORGANISM: Apis florea

<400> SEQUENCE: 10

Trp Ile Gly Ala Ile Leu Lys Val Leu Ala Thr Gly Leu Pro Thr Leu
1               5                   10                  15

Ile Ser Trp Ile Lys Asn Lys Arg Lys Gln
            20                  25

<210> SEQ ID NO 11
<211> LENGTH: 26
<212> TYPE: PRT
<213> ORGANISM: Apis florea

<400> SEQUENCE: 11

Tyr Ile Gly Ala Ile Leu Lys Val Leu Ala Thr Gly Leu Pro Thr Leu
1               5                   10                  15

Ile Ser Trp Ile Lys Asn Lys Arg Lys Gln
            20                  25

<210> SEQ ID NO 12
<211> LENGTH: 26
<212> TYPE: PRT
<213> ORGANISM: Apis florea

<400> SEQUENCE: 12

Gly Ile Gly Ala Ile Leu Lys Val Leu Ala Cys Gly Leu Pro Thr Leu
1               5                   10                  15

Ile Ser Trp Ile Lys Asn Lys Arg Lys Gln
            20                  25

<210> SEQ ID NO 13
<211> LENGTH: 26
<212> TYPE: PRT
<213> ORGANISM: Apis florea

<400> SEQUENCE: 13

Gly Ile Gly Ala Ile Leu Lys Val Leu Ala Thr Leu Leu Pro Thr Leu
1               5                   10                  15

Ile Ser Trp Ile Lys Asn Lys Arg Lys Gln
            20                  25

<210> SEQ ID NO 14
<211> LENGTH: 26
<212> TYPE: PRT
<213> ORGANISM: Apis florea

<400> SEQUENCE: 14

Gly Ile Gly Ala Ile Leu Lys Val Leu Ala Thr Trp Leu Pro Thr Leu
1               5                   10                  15

Ile Ser Trp Ile Lys Asn Lys Arg Lys Gln
            20                  25

<210> SEQ ID NO 15
<211> LENGTH: 26
<212> TYPE: PRT
<213> ORGANISM: Apis florea

<400> SEQUENCE: 15

Gly Ile Gly Ala Ile Leu Lys Val Leu Ala Thr Gly Leu Pro Thr Leu
1               5                   10                  15

Ile Ser Trp Ile Lys Thr Lys Arg Lys Gln
            20                  25

<210> SEQ ID NO 16
<211> LENGTH: 26
<212> TYPE: PRT
<213> ORGANISM: Apis florea

<400> SEQUENCE: 16

Tyr Ile Gly Ala Ile Leu Asn Val Leu Ala Thr Gly Leu Pro Thr Leu
1               5                   10                  15

Ile Ser Trp Ile Lys Asn Lys Arg Lys Gln
            20                  25

<210> SEQ ID NO 17
<211> LENGTH: 26
<212> TYPE: PRT
<213> ORGANISM: Apis florea

<400> SEQUENCE: 17

Tyr Ile Gly Ala Ile Leu Ala Val Leu Ala Thr Gly Leu Pro Thr Leu
1               5                   10                  15

Ile Ser Trp Ile Lys Asn Lys Arg Lys Gln
            20                  25

<210> SEQ ID NO 18
<211> LENGTH: 26
<212> TYPE: PRT
<213> ORGANISM: Apis florea

<400> SEQUENCE: 18

Leu Ile Gly Ala Ile Leu Ser Val Leu Ala Thr Gly Leu Pro Thr Leu
1               5                   10                  15

Ile Ser Trp Ile Lys Asn Lys Arg Lys Gln
            20                  25

<210> SEQ ID NO 19
<211> LENGTH: 26
<212> TYPE: PRT
<213> ORGANISM: Apis florea

<400> SEQUENCE: 19

Leu Ile Gly Ala Ile Leu Arg Val Leu Ala Thr Gly Leu Pro Thr Leu
1               5                   10                  15

Ile Ser Trp Ile Lys Asn Lys Arg Lys Gln
            20                  25

<210> SEQ ID NO 20
<211> LENGTH: 26
<212> TYPE: PRT
<213> ORGANISM: Apis florea

<400> SEQUENCE: 20

Leu Ile Gly Ala Ile Leu His Val Leu Ala Thr Gly Leu Pro Thr Leu

-continued

```
                1               5                  10                  15
Ile Ser Trp Ile Lys Asn Lys Arg Lys Gln
            20                  25

<210> SEQ ID NO 21
<211> LENGTH: 26
<212> TYPE: PRT
<213> ORGANISM: Apis florea

<400> SEQUENCE: 21

Leu Ile Gly Ala Ile Leu Lys Val Leu Ala Cys Gly Leu Pro Thr Leu
1               5                  10                  15

Ile Ser Trp Ile Lys Asn Lys Arg Lys Gln
            20                  25

<210> SEQ ID NO 22
<211> LENGTH: 26
<212> TYPE: PRT
<213> ORGANISM: Apis florea

<400> SEQUENCE: 22

Leu Ile Gly Ala Ile Leu Lys Val Leu Ala Thr Leu Leu Pro Thr Leu
1               5                  10                  15

Ile Ser Trp Ile Lys Asn Lys Arg Lys Gln
            20                  25

<210> SEQ ID NO 23
<211> LENGTH: 26
<212> TYPE: PRT
<213> ORGANISM: Apis florea

<400> SEQUENCE: 23

Tyr Ile Gly Ala Ile Leu Lys Val Leu Ala Thr Gly Leu Leu Thr Leu
1               5                  10                  15

Ile Ser Trp Ile Lys Asn Lys Arg Lys Gln
            20                  25

<210> SEQ ID NO 24
<211> LENGTH: 26
<212> TYPE: PRT
<213> ORGANISM: Apis florea

<400> SEQUENCE: 24

Leu Ile Gly Ala Ile Leu Lys Val Leu Ala Thr Gly Leu Pro Cys Leu
1               5                  10                  15

Ile Ser Trp Ile Lys Asn Lys Arg Lys Gln
            20                  25

<210> SEQ ID NO 25
<211> LENGTH: 26
<212> TYPE: PRT
<213> ORGANISM: Apis florea

<400> SEQUENCE: 25

Leu Ile Gly Ala Ile Leu Lys Val Leu Ala Thr Gly Leu Pro Thr Leu
1               5                  10                  15

Ile Cys Trp Ile Lys Asn Lys Arg Lys Gln
            20                  25

<210> SEQ ID NO 26
<211> LENGTH: 26
<212> TYPE: PRT
```

-continued

<213> ORGANISM: Apis florea

<400> SEQUENCE: 26

Tyr Ile Gly Ala Ile Leu Lys Val Leu Ala Thr Gly Leu Pro Thr Leu
1               5                   10                  15
Ile Ser Ala Ile Lys Asn Lys Arg Lys Gln
            20                  25

<210> SEQ ID NO 27
<211> LENGTH: 26
<212> TYPE: PRT
<213> ORGANISM: Apis florea

<400> SEQUENCE: 27

Gly Ile Gly Ala Ile Leu Lys Val Leu Ala Cys Gly Leu Pro Thr Leu
1               5                   10                  15
Ile Ser Trp Leu Lys Asn Lys Arg Lys Gln
            20                  25

<210> SEQ ID NO 28
<211> LENGTH: 26
<212> TYPE: PRT
<213> ORGANISM: Apis florea

<400> SEQUENCE: 28

Tyr Ile Gly Ala Ile Leu Lys Val Leu Ala Thr Gly Leu Pro Thr Leu
1               5                   10                  15
Ile Ser Trp Ile Ala Asn Lys Arg Lys Gln
            20                  25

<210> SEQ ID NO 29
<211> LENGTH: 26
<212> TYPE: PRT
<213> ORGANISM: Apis florea

<400> SEQUENCE: 29

Tyr Ile Gly Ala Ile Leu Lys Val Leu Ala Thr Gly Leu Pro Thr Leu
1               5                   10                  15
Ile Ser Trp Ile Lys Asn Ala Arg Lys Gln
            20                  25

<210> SEQ ID NO 30
<211> LENGTH: 26
<212> TYPE: PRT
<213> ORGANISM: Apis florea

<400> SEQUENCE: 30

Leu Ile Gly Ala Ile Leu Lys Val Leu Ala Thr Gly Leu Pro Thr Leu
1               5                   10                  15
Ile Ser Trp Ile Lys Asn Lys Ala Lys Gln
            20                  25

<210> SEQ ID NO 31
<211> LENGTH: 26
<212> TYPE: PRT
<213> ORGANISM: Apis florea

<400> SEQUENCE: 31

Tyr Ile Gly Ala Ile Leu Lys Val Leu Ala Thr Gly Leu Pro Thr Leu
1               5                   10                  15
Ile Ser Trp Ile Lys Asn Lys Arg Ala Gln
            20                  25

<210> SEQ ID NO 32
<211> LENGTH: 26
<212> TYPE: PRT
<213> ORGANISM: Apis florea

<400> SEQUENCE: 32

Tyr Ile Gly Ala Ile Leu Lys Val Leu Ala Thr Gly Leu Pro Thr Leu
1               5                   10                  15

Ile Ser Trp Ile Lys Asn Lys Arg Lys Cys
            20                  25

<210> SEQ ID NO 33
<211> LENGTH: 26
<212> TYPE: PRT
<213> ORGANISM: Apis florea

<400> SEQUENCE: 33

Leu Leu Gly Ala Ile Leu Lys Val Leu Ala Cys Gly Leu Pro Thr Leu
1               5                   10                  15

Ile Ser Trp Ile Lys Asn Lys Arg Lys Gln
            20                  25

<210> SEQ ID NO 34
<211> LENGTH: 26
<212> TYPE: PRT
<213> ORGANISM: Apis florea

<400> SEQUENCE: 34

Leu Ile Gly Ala Leu Leu Lys Val Leu Ala Cys Gly Leu Pro Thr Leu
1               5                   10                  15

Ile Ser Trp Ile Lys Asn Lys Arg Lys Gln
            20                  25

<210> SEQ ID NO 35
<211> LENGTH: 26
<212> TYPE: PRT
<213> ORGANISM: Apis florea

<400> SEQUENCE: 35

Tyr Ile Gly Ala Ile Leu Ala Val Leu Ala Thr Gly Leu Pro Thr Leu
1               5                   10                  15

Ile Ser Trp Ile Ala Asn Lys Arg Lys Gln
            20                  25

<210> SEQ ID NO 36
<211> LENGTH: 26
<212> TYPE: PRT
<213> ORGANISM: Apis florea

<400> SEQUENCE: 36

Tyr Ile Gly Ala Ile Leu Ala Val Leu Ala Thr Gly Leu Pro Thr Leu
1               5                   10                  15

Ile Ser Trp Ile Lys Asn Ala Arg Lys Gln
            20                  25

<210> SEQ ID NO 37
<211> LENGTH: 26
<212> TYPE: PRT
<213> ORGANISM: Apis florea

<400> SEQUENCE: 37

```
Leu Ile Gly Ala Ile Leu Lys Val Leu Ala Cys Gly Leu Pro Thr Leu
1               5                   10                  15

Leu Ser Trp Ile Lys Asn Lys Arg Lys Gln
            20                  25
```

<210> SEQ ID NO 38
<211> LENGTH: 26
<212> TYPE: PRT
<213> ORGANISM: Apis florea

<400> SEQUENCE: 38

```
Leu Ile Gly Ala Ile Leu Lys Val Leu Ala Cys Gly Leu Pro Thr Leu
1               5                   10                  15

Ile Cys Trp Ile Lys Asn Lys Arg Lys Gln
            20                  25
```

<210> SEQ ID NO 39
<211> LENGTH: 26
<212> TYPE: PRT
<213> ORGANISM: Apis florea

<400> SEQUENCE: 39

```
Gly Ile Gly Ala Ile Leu Lys Val Leu Ala Cys Gly Leu Pro Gly Leu
1               5                   10                  15

Ile Gly Trp Ile Lys Asn Lys Arg Lys Gln
            20                  25
```

<210> SEQ ID NO 40
<211> LENGTH: 26
<212> TYPE: PRT
<213> ORGANISM: Apis florea

<400> SEQUENCE: 40

```
Gly Ile Gly Ala Ile Leu Lys Val Leu Ala Cys Gly Leu Pro Ala Leu
1               5                   10                  15

Ile Ala Trp Ile Lys Asn Lys Arg Lys Gln
            20                  25
```

<210> SEQ ID NO 41
<211> LENGTH: 26
<212> TYPE: PRT
<213> ORGANISM: Apis florea

<400> SEQUENCE: 41

```
Tyr Ile Gly Ala Ile Leu Ala Val Leu Ala Thr Gly Leu Pro Thr Leu
1               5                   10                  15

Ile Ser Trp Ile Ala Asn Ala Arg Lys Gln
            20                  25
```

<210> SEQ ID NO 42
<211> LENGTH: 26
<212> TYPE: PRT
<213> ORGANISM: Apis florea

<400> SEQUENCE: 42

```
Tyr Ile Ala Ala Ile Leu Lys Val Leu Ala Ala Ala Leu Ala Thr Leu
1               5                   10                  15

Ile Ser Trp Ile Lys Asn Lys Arg Lys Gln
            20                  25
```

<210> SEQ ID NO 43
<211> LENGTH: 26

<212> TYPE: PRT
<213> ORGANISM: Apis florea

<400> SEQUENCE: 43

Leu Leu Gly Ala Leu Leu Lys Val Leu Ala Thr Gly Leu Pro Thr Leu
1               5                   10                  15

Leu Ser Trp Leu Lys Asn Lys Arg Lys Gln
            20                  25

<210> SEQ ID NO 44
<211> LENGTH: 34
<212> TYPE: PRT
<213> ORGANISM: Apis florea

<400> SEQUENCE: 44

Leu Asn Leu Glu Gly Ala Asn Leu Glu Leu Lys Val Leu Ala Thr Gly
1               5                   10                  15

Leu Pro Thr Leu Asn Leu Glu Ser Trp Asn Leu Glu Lys Asn Lys Arg
            20                  25                  30

Lys Gln

<210> SEQ ID NO 45
<211> LENGTH: 26
<212> TYPE: PRT
<213> ORGANISM: Apis florea

<400> SEQUENCE: 45

Leu Val Gly Ala Val Leu Lys Val Leu Ala Thr Gly Leu Pro Thr Leu
1               5                   10                  15

Val Ser Trp Val Lys Asn Lys Arg Lys Gln
            20                  25

<210> SEQ ID NO 46
<211> LENGTH: 26
<212> TYPE: PRT
<213> ORGANISM: Apis florea

<400> SEQUENCE: 46

Gly Leu Gly Ala Leu Leu Lys Val Leu Ala Cys Gly Leu Pro Thr Leu
1               5                   10                  15

Leu Ser Trp Leu Lys Asn Lys Arg Lys Gln
            20                  25

<210> SEQ ID NO 47
<211> LENGTH: 34
<212> TYPE: PRT
<213> ORGANISM: Apis florea

<400> SEQUENCE: 47

Gly Asn Leu Glu Gly Ala Asn Leu Glu Leu Lys Val Leu Ala Cys Gly
1               5                   10                  15

Leu Pro Thr Leu Asn Leu Glu Ser Trp Asn Leu Glu Lys Asn Lys Arg
            20                  25                  30

Lys Gln

<210> SEQ ID NO 48
<211> LENGTH: 31
<212> TYPE: PRT
<213> ORGANISM: Apis florea

<400> SEQUENCE: 48

-continued

Cys Glu Asp Asp Leu Leu Gly Ala Ile Leu Lys Val Leu Ala Thr
1               5                   10                  15

Gly Leu Pro Thr Leu Ile Ser Trp Ile Lys Asn Lys Arg Lys Gln
            20                  25                  30

<210> SEQ ID NO 49
<211> LENGTH: 31
<212> TYPE: PRT
<213> ORGANISM: Apis florea

<400> SEQUENCE: 49

Cys Leu Val Val Leu Ile Val Val Ala Ile Leu Lys Val Leu Ala Thr
1               5                   10                  15

Gly Leu Pro Thr Leu Ile Ser Trp Ile Lys Asn Lys Arg Lys Gln
            20                  25                  30

<210> SEQ ID NO 50
<211> LENGTH: 26
<212> TYPE: PRT
<213> ORGANISM: Apis mellifera

<400> SEQUENCE: 50

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 51
<211> LENGTH: 27
<212> TYPE: PRT
<213> ORGANISM: Apis florea

<400> SEQUENCE: 51

Cys Leu Ile Gly Ala Ile Leu Lys Val Leu Ala Thr Gly Leu Pro Thr
1               5                   10                  15

Leu Ile Ser Trp Ile Lys Asn Lys Arg Lys Gln
            20                  25

<210> SEQ ID NO 52
<211> LENGTH: 29
<212> TYPE: PRT
<213> ORGANISM: Apis florea

<400> SEQUENCE: 52

Cys Asn Leu Glu Ile Gly Ala Ile Leu Lys Val Leu Ala Thr Gly Leu
1               5                   10                  15

Pro Thr Leu Ile Ser Trp Ile Lys Asn Lys Arg Lys Gln
            20                  25

<210> SEQ ID NO 53
<211> LENGTH: 27
<212> TYPE: PRT
<213> ORGANISM: Apis florea

<400> SEQUENCE: 53

Gly Leu Ile Gly Ala Ile Leu Lys Val Leu Ala Thr Gly Leu Pro Thr
1               5                   10                  15

Leu Ile Ser Trp Ile Lys Asn Lys Arg Lys Gln
            20                  25

<210> SEQ ID NO 54
<211> LENGTH: 27

-continued

```
<212> TYPE: PRT
<213> ORGANISM: Apis florea

<400> SEQUENCE: 54

Leu Leu Ile Gly Ala Ile Leu Lys Val Leu Ala Thr Gly Leu Pro Thr
 1               5                  10                  15

Leu Ile Ser Trp Ile Lys Asn Lys Arg Lys Gln
             20                  25

<210> SEQ ID NO 55
<211> LENGTH: 29
<212> TYPE: PRT
<213> ORGANISM: Apis florea

<400> SEQUENCE: 55

Lys Leu Lys Leu Ile Gly Ala Ile Leu Lys Val Leu Ala Thr Gly Leu
 1               5                  10                  15

Pro Thr Leu Ile Ser Trp Ile Lys Asn Lys Arg Lys Gln
             20                  25

<210> SEQ ID NO 56
<211> LENGTH: 29
<212> TYPE: PRT
<213> ORGANISM: Apis florea

<400> SEQUENCE: 56

Lys Leu Lys Tyr Ile Gly Ala Ile Leu Lys Val Leu Ala Thr Gly Leu
 1               5                  10                  15

Pro Thr Leu Ile Ser Trp Ile Lys Asn Lys Arg Lys Gln
             20                  25

<210> SEQ ID NO 57
<211> LENGTH: 30
<212> TYPE: PRT
<213> ORGANISM: Apis florea

<400> SEQUENCE: 57

Cys Lys Leu Lys Leu Ile Gly Ala Ile Leu Lys Val Leu Ala Thr Gly
 1               5                  10                  15

Leu Pro Thr Leu Ile Ser Trp Ile Lys Asn Lys Arg Lys Gln
             20                  25                  30

<210> SEQ ID NO 58
<211> LENGTH: 32
<212> TYPE: PRT
<213> ORGANISM: Apis florea

<400> SEQUENCE: 58

Cys Lys Leu Lys Asn Leu Glu Ile Gly Ala Ile Leu Lys Val Leu Ala
 1               5                  10                  15

Thr Gly Leu Pro Thr Leu Ile Ser Trp Ile Lys Asn Lys Arg Lys Gln
             20                  25                  30

<210> SEQ ID NO 59
<211> LENGTH: 30
<212> TYPE: PRT
<213> ORGANISM: Apis florea

<400> SEQUENCE: 59

Gly Lys Leu Lys Leu Ile Gly Ala Ile Leu Lys Val Leu Ala Thr Gly
 1               5                  10                  15

Leu Pro Thr Leu Ile Ser Trp Ile Lys Asn Lys Arg Lys Gln
```

<210> SEQ ID NO 60
<211> LENGTH: 30
<212> TYPE: PRT
<213> ORGANISM: Apis florea

<400> SEQUENCE: 60

Cys Pro Ala Asn Leu Ile Gly Ala Ile Leu Lys Val Leu Ala Thr Gly
1               5                   10                  15

Leu Pro Thr Leu Ile Ser Trp Ile Lys Asn Lys Arg Lys Gln
            20                  25                  30

<210> SEQ ID NO 61
<211> LENGTH: 31
<212> TYPE: PRT
<213> ORGANISM: Apis florea

<400> SEQUENCE: 61

Asp Glu Pro Leu Arg Ala Ile Gly Ala Ile Leu Lys Val Leu Ala Thr
1               5                   10                  15

Gly Leu Pro Thr Leu Ile Ser Trp Ile Lys Asn Lys Arg Lys Gln
            20                  25                  30

<210> SEQ ID NO 62
<211> LENGTH: 27
<212> TYPE: PRT
<213> ORGANISM: Apis florea

<400> SEQUENCE: 62

Gly Ile Gly Ala Ile Leu Lys Val Leu Ala Thr Gly Leu Pro Thr Leu
1               5                   10                  15

Ile Ser Trp Ile Lys Asn Lys Arg Lys Gln Cys
            20                  25

<210> SEQ ID NO 63
<211> LENGTH: 27
<212> TYPE: PRT
<213> ORGANISM: Apis florea

<400> SEQUENCE: 63

Leu Ile Gly Ala Ile Leu Lys Val Leu Ala Thr Gly Leu Pro Thr Leu
1               5                   10                  15

Ile Ser Trp Ile Lys Asn Lys Arg Lys Gln Cys
            20                  25

<210> SEQ ID NO 64
<211> LENGTH: 29
<212> TYPE: PRT
<213> ORGANISM: Apis florea

<400> SEQUENCE: 64

Asn Leu Glu Ile Gly Ala Ile Leu Lys Val Leu Ala Thr Gly Leu Pro
1               5                   10                  15

Thr Leu Ile Ser Trp Ile Lys Asn Lys Arg Lys Gln Cys
            20                  25

<210> SEQ ID NO 65
<211> LENGTH: 30
<212> TYPE: PRT
<213> ORGANISM: Apis florea

<400> SEQUENCE: 65

```
Leu Ile Gly Ala Ile Leu Lys Val Leu Ala Thr Gly Leu Pro Thr Leu
1               5                   10                  15

Ile Ser Trp Ile Lys Asn Lys Arg Lys Gln Lys Leu Lys Cys
                20                  25                  30
```

<210> SEQ ID NO 66
<211> LENGTH: 34
<212> TYPE: PRT
<213> ORGANISM: Apis florea

<400> SEQUENCE: 66

```
Tyr Ile Gly Ala Ile Leu Lys Val Leu Ala Thr Gly Leu Pro Thr Leu
1               5                   10                  15

Ile Ser Trp Ile Lys Asn Lys Arg Lys Gln Pro Leu Gly Ile Ala Gly
                20                  25                  30

Gln Cys
```

<210> SEQ ID NO 67
<211> LENGTH: 31
<212> TYPE: PRT
<213> ORGANISM: Apis florea

<400> SEQUENCE: 67

```
Leu Ile Gly Ala Ile Leu Lys Val Leu Ala Thr Gly Leu Pro Thr Leu
1               5                   10                  15

Ile Ser Trp Ile Lys Asn Lys Arg Lys Gln Lys Lys Lys Lys Lys
                20                  25                  30
```

<210> SEQ ID NO 68
<211> LENGTH: 31
<212> TYPE: PRT
<213> ORGANISM: Apis florea

<400> SEQUENCE: 68

```
Tyr Ile Gly Ala Ile Leu Lys Val Leu Ala Thr Gly Leu Pro Thr Leu
1               5                   10                  15

Ile Ser Trp Ile Lys Asn Lys Arg Lys Gln Gly Phe Lys Gly Cys
                20                  25                  30
```

<210> SEQ ID NO 69
<211> LENGTH: 30
<212> TYPE: PRT
<213> ORGANISM: Apis florea

<400> SEQUENCE: 69

```
Cys Phe Lys Leu Ile Gly Ala Ile Leu Lys Val Leu Ala Thr Gly Leu
1               5                   10                  15

Pro Thr Leu Ile Ser Trp Ile Lys Asn Lys Arg Lys Gln Cys
                20                  25                  30
```

<210> SEQ ID NO 70
<211> LENGTH: 25
<212> TYPE: PRT
<213> ORGANISM: Apis florea

<400> SEQUENCE: 70

```
Phe Gly Ala Ile Leu Lys Val Leu Ala Thr Gly Leu Pro Thr Leu Ile
1               5                   10                  15

Ser Trp Ile Lys Asn Lys Arg Lys Gln
                20                  25
```

-continued

<210> SEQ ID NO 71
<211> LENGTH: 23
<212> TYPE: PRT
<213> ORGANISM: Apis florea

<400> SEQUENCE: 71

Leu Ile Gly Ala Ile Leu Lys Val Leu Ala Thr Gly Leu Pro Thr Leu
1               5                   10                  15

Ile Ser Trp Ile Lys Asn Lys
            20

<210> SEQ ID NO 72
<211> LENGTH: 21
<212> TYPE: PRT
<213> ORGANISM: Apis mellifera

<400> SEQUENCE: 72

Leu Ile Gly Ala Val Leu Lys Val Leu Thr Thr Gly Leu Pro Ala Leu
1               5                   10                  15

Ile Ser Trp Ile Lys
            20

<210> SEQ ID NO 73
<211> LENGTH: 23
<212> TYPE: PRT
<213> ORGANISM: Apis mellifera

<400> SEQUENCE: 73

Leu Ile Gly Ala Val Leu Lys Val Leu Thr Thr Gly Leu Pro Ala Leu
1               5                   10                  15

Ile Ser Trp Ile Lys Gly Glu
            20

<210> SEQ ID NO 74
<211> LENGTH: 26
<212> TYPE: PRT
<213> ORGANISM: Apis florea

<400> SEQUENCE: 74

Gln Lys Arg Lys Asn Lys Ile Trp Ser Ile Leu Thr Pro Leu Gly Thr
1               5                   10                  15

Ala Leu Val Lys Leu Ile Ala Gly Ile Leu
            20                  25

<210> SEQ ID NO 75
<211> LENGTH: 29
<212> TYPE: PRT
<213> ORGANISM: Apis florea

<400> SEQUENCE: 75

Lys Leu Lys Gln Lys Arg Lys Asn Lys Ile Trp Ser Ile Leu Thr Pro
1               5                   10                  15

Leu Gly Thr Ala Leu Val Lys Leu Ile Ala Gly Ile Leu
            20                  25

<210> SEQ ID NO 76
<211> LENGTH: 27
<212> TYPE: PRT
<213> ORGANISM: Apis mellifera

<400> SEQUENCE: 76

Gly Ile Gly Ala Val Leu Lys Val Leu Thr Thr Gly Leu Pro Ala Leu
1               5                   10                  15

```
                1               5                   10                  15
Ile Ser Trp Ile Ser Arg Lys Lys Arg Gln Gln
                20                  25

<210> SEQ ID NO 77
<211> LENGTH: 25
<212> TYPE: PRT
<213> ORGANISM: Apis mellifera

<400> SEQUENCE: 77

Gly Ile Gly Ala Arg Leu Lys Val Leu Thr Thr Gly Leu Pro Arg Ile
1               5                   10                  15

Ser Trp Ile Lys Arg Lys Arg Gln Gln
                20                  25

<210> SEQ ID NO 78
<211> LENGTH: 26
<212> TYPE: PRT
<213> ORGANISM: Apis florea

<400> SEQUENCE: 78

Gly Ile Gly Ala Ile Leu Lys Val Leu Ser Thr Gly Leu Pro Ala Leu
1               5                   10                  15

Ile Ser Trp Ile Lys Arg Lys Arg Gln Glu
                20                  25

<210> SEQ ID NO 79
<211> LENGTH: 26
<212> TYPE: PRT
<213> ORGANISM: Apis mellifera

<400> SEQUENCE: 79

Gly Ile Gly Ala Val Leu Lys Val Leu Thr Thr Gly Leu Pro Ala Leu
1               5                   10                  15

Ile Gly Trp Ile Lys Arg Lys Arg Gln Gln
                20                  25

<210> SEQ ID NO 80
<211> LENGTH: 26
<212> TYPE: PRT
<213> ORGANISM: Apis mellifera

<400> SEQUENCE: 80

Gly Ile Gly Ala Val Leu Lys Val Leu Ala Thr Gly Leu Pro Ala Leu
1               5                   10                  15

Ile Ser Trp Ile Lys Arg Lys Arg Gln Gln
                20                  25

<210> SEQ ID NO 81
<211> LENGTH: 26
<212> TYPE: PRT
<213> ORGANISM: Apis mellifera

<400> SEQUENCE: 81

Gly Ile Gly Ala Val Leu Lys Val Leu Ser Thr Gly Leu Pro Ala Leu
1               5                   10                  15

Ile Ser Trp Ile Lys Arg Lys Arg Gln Gln
                20                  25

<210> SEQ ID NO 82
<211> LENGTH: 26
<212> TYPE: PRT
```

<213> ORGANISM: Apis florea

<400> SEQUENCE: 82

Gly Ile Gly Ala Ile Leu Arg Val Leu Ala Thr Gly Leu Pro Thr Leu
1               5                   10                  15

Ile Ser Trp Ile Lys Asn Lys Arg Lys Gln
            20                  25

<210> SEQ ID NO 83
<211> LENGTH: 26
<212> TYPE: PRT
<213> ORGANISM: Apis florea

<400> SEQUENCE: 83

Gly Ile Gly Ala Ile Leu Lys Val Leu Ala Thr Gly Leu Pro Thr Leu
1               5                   10                  15

Ile Ser Trp Ile Lys Arg Lys Arg Lys Gln
            20                  25

<210> SEQ ID NO 84
<211> LENGTH: 26
<212> TYPE: PRT
<213> ORGANISM: Apis florea

<400> SEQUENCE: 84

Gly Ile Gly Ala Ile Leu Lys Val Leu Ala Thr Gly Leu Pro Thr Leu
1               5                   10                  15

Ile Ser Trp Ile Lys Lys Lys Lys Gln Gln
            20                  25

<210> SEQ ID NO 85
<211> LENGTH: 32
<212> TYPE: PRT
<213> ORGANISM: Apis florea

<400> SEQUENCE: 85

Gly Ile Gly Ala Ile Leu Lys Val Leu Ala Thr Gly Leu Pro Thr Leu
1               5                   10                  15

Ile Ser Trp Ile Lys Asn Lys Arg Lys Gln Gly Ser Lys Lys Lys Lys
            20                  25                  30

<210> SEQ ID NO 86
<211> LENGTH: 28
<212> TYPE: PRT
<213> ORGANISM: Apis florea

<400> SEQUENCE: 86

Lys Lys Gly Ile Gly Ala Ile Leu Lys Val Leu Ala Thr Gly Leu Pro
1               5                   10                  15

Thr Leu Ile Ser Trp Ile Lys Asn Lys Arg Lys Gln
            20                  25

<210> SEQ ID NO 87
<211> LENGTH: 26
<212> TYPE: PRT
<213> ORGANISM: Apis florea

<400> SEQUENCE: 87

Gly Ile Gly Ala Ile Leu Glu Val Leu Ala Thr Gly Leu Pro Thr Leu
1               5                   10                  15

Ile Ser Trp Ile Lys Asn Lys Arg Lys Gln
            20                  25

```
<210> SEQ ID NO 88
<211> LENGTH: 24
<212> TYPE: PRT
<213> ORGANISM: Apis mellifera

<400> SEQUENCE: 88

Gly Ile Gly Ala Val Leu Lys Val Leu Thr Thr Gly Leu Pro Ala Leu
1               5                   10                  15

Ile Ser Trp Ile Lys Arg Lys Arg
            20

<210> SEQ ID NO 89
<211> LENGTH: 22
<212> TYPE: PRT
<213> ORGANISM: Apis mellifera

<400> SEQUENCE: 89

Gly Ile Gly Ala Val Leu Lys Val Leu Thr Thr Gly Leu Pro Ala Leu
1               5                   10                  15

Ile Ser Trp Ile Lys Arg
            20

<210> SEQ ID NO 90
<211> LENGTH: 26
<212> TYPE: PRT
<213> ORGANISM: Apis mellifera

<400> SEQUENCE: 90

Cys Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 91
<211> LENGTH: 26
<212> TYPE: PRT
<213> ORGANISM: Apis mellifera

<400> SEQUENCE: 91

Gln Gln Arg Lys Arg Lys Ile Trp Ser Ile Leu Ala Pro Leu Gly Thr
1               5                   10                  15

Thr Leu Val Lys Leu Val Ala Gly Ile Gly
            20                  25

<210> SEQ ID NO 92
<211> LENGTH: 26
<212> TYPE: PRT
<213> ORGANISM: Apis mellifera

<400> SEQUENCE: 92

Gln Gln Arg Lys Arg Lys Ile Trp Ser Ile Leu Ala Pro Leu Gly Thr
1               5                   10                  15

Thr Leu Val Lys Leu Val Ala Gly Ile Cys
            20                  25

<210> SEQ ID NO 93
<211> LENGTH: 26
<212> TYPE: PRT
<213> ORGANISM: Apis mellifera

<400> SEQUENCE: 93
```

```
Gln Gln Lys Lys Lys Ile Trp Ser Ile Leu Ala Pro Leu Gly Thr
1               5                   10                  15
Thr Leu Val Lys Leu Val Ala Gly Ile Cys
            20                  25

<210> SEQ ID NO 94
<211> LENGTH: 26
<212> TYPE: PRT
<213> ORGANISM: Apis florea

<400> SEQUENCE: 94

Gln Lys Arg Lys Asn Lys Ile Trp Ser Ile Leu Thr Pro Leu Gly Thr
1               5                   10                  15
Ala Leu Val Lys Leu Ile Ala Gly Ile Gly
            20                  25

<210> SEQ ID NO 95
<211> LENGTH: 26
<212> TYPE: PRT
<213> ORGANISM: Apis mellifera

<400> SEQUENCE: 95

Gln Gln Arg Lys Arg Lys Ile Trp Ser Ile Leu Ala Ala Leu Gly Thr
1               5                   10                  15
Thr Leu Val Lys Leu Val Ala Gly Ile Cys
            20                  25

<210> SEQ ID NO 96
<211> LENGTH: 26
<212> TYPE: PRT
<213> ORGANISM: Apis florea

<400> SEQUENCE: 96

Gln Lys Arg Lys Asn Lys Ile Trp Ser Ile Leu Thr Pro Leu Gly Thr
1               5                   10                  15
Ala Leu Val Lys Leu Ile Ala Gly Ile Gly
            20                  25

<210> SEQ ID NO 97
<211> LENGTH: 20
<212> TYPE: DNA
<213> ORGANISM: Mus musculus

<400> SEQUENCE: 97
gcaaaggcgu gccaacucat                                          20

<210> SEQ ID NO 98
<211> LENGTH: 21
<212> TYPE: DNA
<213> ORGANISM: Mus musculus

<400> SEQUENCE: 98
tgaguuggca cgccuuugct t                                        21

<210> SEQ ID NO 99
<211> LENGTH: 21
<212> TYPE: DNA
<213> ORGANISM: Mus musculus

<400> SEQUENCE: 99
ggaucaucuc aagucuuact t                                        21
```

-continued

```
<210> SEQ ID NO 100
<211> LENGTH: 21
<212> TYPE: DNA
<213> ORGANISM: Mus musculus

<400> SEQUENCE: 100
guaagacuug agaugaucct t                                                    21

<210> SEQ ID NO 101
<211> LENGTH: 24
<212> TYPE: DNA
<213> ORGANISM: Macaca fascicularis

<400> SEQUENCE: 101
uuagguuggu gaauggagcu cagt                                                 24

<210> SEQ ID NO 102
<211> LENGTH: 21
<212> TYPE: DNA
<213> ORGANISM: Macaca fascicularis

<400> SEQUENCE: 102
cugagcucca uucaccaact t                                                    21

<210> SEQ ID NO 103
<211> LENGTH: 21
<212> TYPE: DNA
<213> ORGANISM: Mus musculus

<400> SEQUENCE: 103
ggaaucuuau auuugaucca a                                                    21

<210> SEQ ID NO 104
<211> LENGTH: 23
<212> TYPE: DNA
<213> ORGANISM: Mus musculus

<400> SEQUENCE: 104
uuggaucaaa uauaagauuc ccu                                                  23

<210> SEQ ID NO 105
<211> LENGTH: 23
<212> TYPE: DNA
<213> ORGANISM: Photinus pyralis

<400> SEQUENCE: 105
uaucuuacgc ugaguacuuc gat                                                  23

<210> SEQ ID NO 106
<211> LENGTH: 21
<212> TYPE: DNA
<213> ORGANISM: Photinus pyralis

<400> SEQUENCE: 106
ucgaaguacu cagcguaagt t                                                    21
```